(12) United States Patent
Price

(10) Patent No.: US 10,513,533 B2
(45) Date of Patent: Dec. 24, 2019

(54) TUNICAMYCIN RELATED COMPOUNDS WITH ANTI-BACTERIAL ACTIVITY

(71) Applicant: The United States of America, as represented by the Secretary of Agriculture, Washington, DC (US)

(72) Inventor: Neil P. Price, Edelstein, IL (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 3 days.

(21) Appl. No.: 15/872,270

(22) Filed: Jan. 16, 2018

(65) Prior Publication Data

US 2018/0208620 A1    Jul. 26, 2018

Related U.S. Application Data

(60) Provisional application No. 62/473,661, filed on Mar. 20, 2017, provisional application No. 62/450,760, filed on Jan. 26, 2017.

(51) Int. Cl.

| | |
|---|---|
| *C07H 19/06* | (2006.01) |
| *A61K 31/7072* | (2006.01) |
| *A61P 31/04* | (2006.01) |
| *A01N 43/54* | (2006.01) |
| *A01N 43/90* | (2006.01) |
| *A61K 31/7034* | (2006.01) |
| *A01N 43/16* | (2006.01) |
| *C07H 19/16* | (2006.01) |
| *A61K 31/7076* | (2006.01) |
| *A01N 57/16* | (2006.01) |
| *A61K 45/06* | (2006.01) |
| *C07H 15/207* | (2006.01) |

(52) U.S. Cl.
CPC ............ *C07H 19/06* (2013.01); *A01N 43/16* (2013.01); *A01N 43/54* (2013.01); *A01N 43/90* (2013.01); *A01N 57/16* (2013.01); *A61K 31/7034* (2013.01); *A61K 31/7072* (2013.01); *A61K 31/7076* (2013.01); *A61P 31/04* (2018.01); *C07H 15/207* (2013.01); *C07H 19/16* (2013.01); *A61K 45/06* (2013.01)

(58) Field of Classification Search
CPC .... C07H 19/16; C07H 19/06; A61K 31/7034; A61K 31/7072; A61K 31/7076; A61K 45/06; A01N 43/16; A01N 43/54; A01N 43/90; A01N 57/16; A61P 31/04
See application file for complete search history.

(56) References Cited

FOREIGN PATENT DOCUMENTS

AU          735205 B2 *  7/2001  ............. C07K 14/47

OTHER PUBLICATIONS

Brown et al., J. Am. Chem. Soc., 1923, 45(11), p. 2702-2708. (Year: 1923).*
Soldo, Blazenka et al., "tagO is involved in the synthesis of all anionic cell-wall polymers in Bacillus subtilis 168," Microbiology, (2002), 148:2079-2087.
Swoboda, Jonathan G. et al., "Discovery of a Small Molecule that Blocks Wall Teichoic Acid Biosynthesis in *Staphylococcus aureus*," ACS Chemical Biology, (2009), 4(10):875-883.
Swoboda, Jonathan G. et al., "Wall Teichoic Acid Function, Biosynthesis, and Inhibition," NIH PA Author Manuscript Chembiochem, (2010),11(1):35-45.
Takatsuki, Akira et al., "Effect of Tunicamycin on the Synthesis of Macromolecules in Cultures of Chick Embryo Fibroblasts Infected With Newcastle Disease Virus," The Journal of Antibiotics, (1971), 24(11):785-794.
Takatsuki, Akira et al., "The Structure of Tunicamycin," Agricultural and Biological Chemistry, (1977), 41(11):2307-2308.
Tran, Anthony T. et al., "A general method for the rapid reduction of alkenes and alkynes using sodium borohydride, acetic acid, and palladium," Tetrahedron Letters, (2009), 50:1817-1819.
Tsvetanova, Billyana C. et al., "Liquid Chromatography-Electrospray Mass Spectrometry of Tunicamycin-Type Antibiotics," Analytical Biochemistry, (2001), 289:147-156.
Tsvetanova, Billyana C. et al., "Biosynthesis of Tunicamycin and Metabolic Origin of the 11-Carbon Dialdose Sugar, Tunicamine*," The Journal of Biological Chemistry, (2002), 277(38):35289-35296.
Vinogradov, Evgueny et al., "Structural elucidation of the extracellular and cell-wall teichoic acids of *Staphylococcus aureus* MN8m, a biofilm forming strain," Science Direct: Carbohydrate Research, (2006), 341:738-743.
Vinogradov, Evgueny et al., "Lipopolysaccharides from Serratia marcescens Possess One or Two 4-Amino-4-deoxy-L-arabinopyranose 1-Phosphate Residues in the Lipid A and D-glycero-D-talo-Oct-2-ulopyranosonic Acid in the Inner Core Region," Chemistry A European Journal, (2006), 12:6692-6700.
Weidenmaier, Christopher et al., "Teichoic acids and related cell-wall glycopolymers in Gram-positive physiology and host interactions," Nature Publishing Group: Microbiology, (2008), 6:276-287.
Price, Neil P.J., "β-Lactams and Tunicamycins A phoenix arises from the ashes of antibiotic-resistance," Tun Pen Slides Revised and Presented, U.S. Dept Agriculture (USDA), Agriculture Research Services, Peoria, IL, (2016), pp. 46 slides.

(Continued)

*Primary Examiner* — Jonathan S Lau
(74) *Attorney, Agent, or Firm* — John D. Fado; Ariel L. Atkinson

(57) ABSTRACT

Tunicamycin related compounds having an acyl chain double bond reduced and/or having an acyl chain double bond and an uracil ring double bond reduced are described as well as methods of making these tunicamycin related compounds. These tunicamycin related compounds are not toxic to eukaryotic cells and can be used to kill Gram-positive bacteria, alone or in combination with other antibiotics. Use of these tunicamycin related compounds to kill Gram-positive bacteria, treat Gram-positive bacterial diseases, and disinfect objects or surfaces are described. In addition, naturally-occurring streptovirudin compounds are not toxic to eukaryotic cells and can be used to kill Gram-positive bacteria, alone or in combination with other antibiotics.

22 Claims, 8 Drawing Sheets

(56) References Cited

OTHER PUBLICATIONS

Wyszynski, Filip J., "Dissecting tunicamycin biosynthesis by genome mining: cloning and heterologous expression of a minimal gene cluster," Chemical Science, (2010),1:581-589.

Hakulinen, Jonna K. et al, "MraY-antibiotic complex reveals details of tunicamycin mode of action," Nature Chemical Biology, (2017), pp. 5.

Hakulinen, Jonna K. et al, "Supplementary Information: MraY-antibiotic complex reveals details of tunicamycin mode-of-action," Additional Data, (2017), pp. 12.

Hirano, Toshihiko et al., "Effect of Tunicamycin on the Biosynthesis of a Glycoprotein Antigen, Contact Site A, in Aggregation-Competent Cells of Dictyostelium discoideum1," J. Biochem, (1982), 92(3): 765-773.

Holtsmark, I. et al., "Original Article: The tomato pathogen *Clavibacter michiganensis* ssp. *michiganensis*: producer of several antimicrobial substances," The Society for Applied Microbiology, Journal of Applied Microbiolgy (2007), 102:416-423.

Kimura, Ken-ichi et al., "Recent advances in antimicrobial nucleoside antibiotics targeting cell wall biosynthesis," Nat. Prod. Rep., (2003), 20:252-273.

Koyama, H. et al., "Tunicamycin-resistant mutations in mouse FM3A cells," Mutation Reseach, Elsevier Biomedical Press, (1982), 96:243-258.

Kukuruzinska, M.A. et al., "Protein Glycosylation in Yeast," Ann. Rev. Biochem, (1987), 56:915-944.

Lee, Sang Ho et al., "Infectious Disease: TarO-specific inhibitors of wall teichoic acid biosynthesis restore β-lactam efficacy against methicillin-resistant *staphylococci*," Science Translational Medicine, (2016), 8(329):1-15.

Lehle, Ludwig et al., "Protein Glycosylation, Conserved from Yeast to Man: A Model Organism Helps Elucidate Congenital Human Diseases," Angew. Chem. Int. Ed., (2006), 45:6802-6818.

Li, Jiakun et al., "A Modular Approach to the Total Synthesis of Tunicamycins," Angew. Chem. Int. Ed., (2015), 54:6618-6621.

Mizuno, Masayuki et al., "An Antibiotic 24010," The Journal of Antibiotics, (1971), 24(12):896-899.

Navarre, William W. et al., "Surface Proteins of Gram-Positive Bacteria and Mechanisms of Their Targeting to the Cell Wall Envelope," Microbiology and Molecular Biology Reviews, (1999), 63(1):174-229.

Neuhas, Francis C. et al., "A Continuum of Anionic Charge: Structures and Functions of D-Alanyl-Teichoic Acids in Gram-Positive Bacteria†," Microbiology and Molecular Biology Reviews, (2003), 67(4): 686-723.

Price, Neil P.J. et al., "Structural determination of symbiotic nodulation factors from the broad host-range *Rhizobium* species NGR234," Elsevier Science Ltd.: Carbohydrate Research, (1996), 289:115-136.

Price, Neil P.J. et al., "Modified tunicamycins with reduced eukaryotic toxicity that enhance the antibacterial activity of β-lactams," The Journal of Antibiotics, (2017), 70:1070-1077.

Price, Neil P.J. et al., "Selective catalytic hydrogenation of the N-acyl and uridyl double bonds in the tunicamycin family of protein N-glycosylation inhibitors," The Journal of Antibiotics, (2017), 70:1122-1128.

Schlag, Martin et al., "Role of *Staphylococcal* wall teichoic acid in targeting the major autolysin Atl," Molecular Microbiology, (2010), 75(4):864-873.

Scocca, Jane R. et al., "Sequence of a cDNA That Specifies the Uridine Diphosphate N-Acetyl-D-glucosamine: Dolichol Phosphate N-Acetylglucosamine-1-phosphate Transferase from Chinese Hamster Ovary Cells*," The Journal of Biological Chemistry, (1990), 265(33):20621-20626.

Amezcua, Kerstin et al., "Development and Evaluation of a Borohydridepalladium System for Selective Reduction of the C=C Bond of α,β-unsaturated Carbonyl Compounds," International Journal of Undergraduate Research and Creative Acitivities, (2015), 7(5):1-11.

Aparici-Espert, Isabel et al., "A Combined Experimental and Theoretical Approach to the Photogeneration of 5,6-Dihydropyrimidin-5-yl Radicals in Nonaqueous Media," The Journal of Organic Chemistry, (2016), 81:4031-4038.

Atta, Houssam M., "Biochemical studies on antibiotic production from *Streptomyces* sp.: Taxonomy, fermentation, isolation and biological properties," Journal of Saudi Chemical Society, (2015), 19:12-22.

Brandish, Phillip E., "Modes of Action of Tunicamycin, Liposidomycin B, and Mureidomycin A: Inhibition of Phospho-N-Acetylmuramyl-Pentapeptide Translocase from *Escherichia coli*," Antimicrobial Agents and Chemotherapy, American Society for Microbiology (1996), 40(7):1640-1644.

Brandish, Phillip E., "Slow Binding Inhibition of Phospho-N-acetylmuramyl-pentapeptidetranslocase (*Escherichia coli*) by Mureidomycin A*," The Journal of biological Chemistry, (1996), 271(13): 7609-7614.

Brown, Stephanie et al., "A Revised Pathway Proposed for *Staphylococcus aureus* Wall Teichoic Acid Biosynthesis Based on In Vitro Reconstitution of the Intracellular Steps", NIH Public Access Author Manuscript, Chem. Biol., (2008), 15(1):12-21.

Brown, Stephanie et al., "Methicillin resistance in *Staphylococcus aureus* requires glycosylated wall teichoic acids," PNAS, (2012), 109(46):18909-18914.

Calamita, Heather G. et al., "Regulation of autolysins in teichuronic acid-containing Bacillus subtilis cells," Molelcular Microbiology, (2002), 44(3): 601-606.

Campbell, Jennifer et al., "Synthetic Lethal Compound Combinations Reveal a Fundamental Connection between Wall Teichoic Acid and Peptidoglycan Biosyntheses in *Staphylococcus aureus*," ACS Chemical Biology, (2011), 6(1): 106-116.

Chen, Wenqing et al., "Research Article: Characterization of the tunicamycin gene cluster unveiling unique steps involved in its biosynthesis," Protein & Cell, (2010), 1(12):1093-1105.

Cockrum, Peter A. et al., High-Performance Liquid Chromatographic Comparison of the Tunicaminyluracil-Based Antibiotics Corynetoxin, Tunicamycin, Streptovirudin and MM 19290, Journal of Chromatography, (1983), 268:245-254.

Doroghazi, James R. et al., "Genome Sequences of Three Tunicamycin-Producing Streptomyces Strains, S. chartreusis NRRL 12338, S. chartreusis NRRL 3882, and S. lysosuperificus ATCC 31396", Journal of Bacteriology, (2011), 193(24):7021-7022.

Duksin, Dan et al., "Changes in surface properties of normal and transformed cells caused by tunicamycin, an inhibitor of protein glycosylation," Proc. Natl. Acad. Sci. USA, (1977), 74(8): 3433-3437.

Eckardt, K., "Tunicamycins, Streptovirudins, and Corynetoxins, A Special Subclass of Nucleoside Antibiotics," Journal of Natural Products, (1983), 46(4):544-550.

Elshikh, Mohammed et al., "Resazurin-based 96-well plate microdilution method for the determination of minimum inhibitory concentration of biosurfactants," Biotechnol Lett, (2016), 38:1015-1019.

Endl, J. et al., "Chemical composition and structure of cell wall teichoic acids of *staphylococci*," Archives of Microbiology, (1983), 135:215-223.

Xia, Liqun et al., "Structures of Alkaloid Biosynthetic Glucosidases Decode Substrate Specificity," ACS Chemical Biology, (2012) 7:226-234.

Farha, Maya A. et al., "Inhibition of WTA Synthesis Blocks the Cooperative Action of PBPs and Sensitizes MRSA to β-L actams," ACS Chemical Biology, (2013) 8:226-233.

\* cited by examiner

Tarocin A:
oxazolidinone series

Tarocin B:
benzimidazole series

TUNICAMYCIN RELATED COMPOUNDS WITH ANTI-BACTERIAL ACTIVITY

CROSS REFERENCE TO RELATED APPLICATION

This application is related to and claims priority to U.S. Patent Application 62/473,661 filed on Mar. 20, 2017 and to U.S. Patent Application 62/450,760 filed on Jan. 26, 2017, the contents of which are incorporated herein.

BACKGROUND OF THE INVENTION

Field of the Invention

This invention relates to single-reduced tunicamycin related compounds and double-reduced tunicamycin related compounds, and methods of making these tunicamycin related compounds. This invention also relates to antibacterial compositions containing a combination of one or more prior art antibiotics and either one or more of the single-reduced tunicamycin related compounds or one or more of the double-reduced tunicamycin related compounds. This invention also relates to the use of these tunicamycin related compounds alone or in combination with other antibiotics to kill bacterial pathogens in animals.

Description Of Related Art

Antimicrobial resistance is considered one of the most serious health threats to both animals and humans. The penicillins were developed by Howard Florey and coworkers in collaboration with the U.S.D.A. in the 1940's, and, despite the rise of resistance, they are still used to treat a wide range of bacteria. Currently, 60% of antibiotics are used for agricultural purposes. The introduction of second generation beta-lactams and of lactam-clavulinic acid combinations initially overcame resistance to some extent, but the rise in pathogens with beta-lactam resistance is now a major concern.

Bacteria often develop resistance to β-lactam antibiotics by expressing a β-lactamase enzyme that attacks the β-lactam ring, thereby rending the antibiotic inactive. Noticeably, *Staphylococcus aureus* lacks a β-lactamase resistance enzyme and thus are unable to degrade β-lactam antibiotics. However, the methicillin-resistant *S. aureus* (MRSA) acquired an alternative protein, penicillin-binding protein (Pbp2a) that inhibits β-lactam antibiotics. Recent studies have demonstrated that MRSA can be rendered susceptible to β-lactam antibiotics again, if the bacterium's teichoic acid biosynthesis is blocked. Several cell wall teichoic acid (WTA) inhibitors exist, such as Targocil, L275, L638, L524, and L555, although most of these compounds have efficacy and toxicity issues. Recently, 2.8 million small molecules were screened for effective WTA inhibitors, and it was determined that two synthetic chemicals (tarocin A (FIG. 1A) and tarocin B (FIG. 1B)) block the first step of teichoic acid synthesis by inhibiting the TarO protein. See, Lee, et al., *Science Translat. Med.* 8:329-329 (ra32 9) (2016). A derivative, tarocin A1, displays complete depletion of the cell wall teichoic acid polymer.

In addition to tarocin A1, tunicamycins display complete depletion of the cell wall teichoic acid polymer. Tunicamycins have known biological activity against eukaryotes by blocking the first step of protein N-glycosylation, ultimately leading to cell death. Tunicamycins inhibit UDP-GlcNAc: dolichol-P GlcNAc-1-P transferase (GPT), a membrane-bound protein that catalyzes the biosynthesis of N-acetylglucosamine-linked dolichol pyrophosphate. This "lipid-linked sugar" is then further modified by subsequent glycosylations, before transfer of the mature N-glycan chain to the Asn-X-Ser/Thr consensus sequence on nascent N-glycoproteins.

Tunicamycins restore β-lactam efficacy against MRSA by inhibiting the formation of the bacterial cell WTA. See, Campbell, et al., *ACS Chem. Biol.* 6:106-116 (2011). Tunicamycins do this by inhibiting TagO, the first enzyme in WTA biosynthesis. Tunicamycins are the more potent than tarocins and improve the antibacterial activity of oxacillin by 64-fold (Lee, et al., (2016)). Lee, et al., (2016) demonstrated that tunicamycins have potent whole-cell WTA pathway-specific inhibitory effects at ≤0.1 mM, whereas tarocin A and tarocin B are notably less active (3 to 26 mM). Furthermore, the tarocins identified by Lee, et al. (2016)) have much less cytotoxicity against human HeLa cells (inhibitory concentration ($IC_{50}$), >100 mM) compared to tunicamycins ($IC_{50}$, 0.2 mM). Tunicamycins are extremely toxic to eukaryotic cells and cannot be used in humans and other animals Tunicamycins are an analog of uridine diphosphate-N-acetylglucosamine (UDP-GlcNAc). See Table 1, infra. As such, they are promiscuous inhibitors of many bacterial glucosyltransferases, such as wall teichoic acid biosynthesis (TagO) and peptidoglycan biosynthesis (MraY) (Mizuno, et al., *J. Antibiot.* 24:896-899 (1971)). Tunicamycins also inhibit enzymes involved in N-linked protein glycosylation in yeast (Alg7) (Kukuruzinska, et al., *Ann. Rev. Biochem.* 56:915-944 (1987)) and in human (DPAGT1) (Lehle et al., *Angew. Chem. Int. Ed. Engl.* 45:6802-18 (2006); Bretthauer, *Curr. Drug Targets* 10:477-82 (2009)). As such, Lee, et al. (2016) states that tarocins and other inhibitors of early wall teichoic acid biosynthesis " . . . may provide an important new strategy to develop Gram-positive bactericidal β-lactam combination agents that are active against methicillin-resistant staphylococci" (Id., p9). Lee, et al. (2016) further states " . . . tunicamycin's cytotoxicity precluded it as a viable chemical starting point to consider as a β-lactam potentiation agent, tarocins provided an attractive alternative therapeutic candidate because they lacked cytotoxicity and intrinsic bioactivity as a single agent." (Id., p3)

Tunicamycins are a family of nucleotide sugar analogs produced by several *Streptomyces* species (Takatsuki, et al., *J. Antibiot.* (Tokyo) 24:215-23 (1971)). The biosynthesis of tunicamycin has been studied previously (Farha, et al., *ACS Chem. Biol.* 8, 226-233 (2012); Endl, et al. (1983)), as has the genomic requirements (Vinogradov, et al. (2006); Weidenmaier and Peschel, *Nat. Rev. Microbiol.* 6:276-287 (2008)), and the mechanism of action (Holland, et al. (2011); Tsvetanova and Price, *Anal. Biochem.* 289:147-156 (2001); Tamura, G., Japan Scientific Press, Tokyo (1982); Kimura and Bugg, *Nat. Prod. Reports* 20:252-273 (2003)). Twelve tunicamycin biosynthetic genes (tunA to tunL) have been identified in *S. chartreusis* NRRL B-3882 and *S. clavuligerus* NRRL 3585 and are also present on the sequenced genome of *Actinosynnema mirum* DSM 44827, although with a truncated tunL gene (Chen, et al *Protein Cell.* 1:1093-105 (2010); Wyszynski, et al, Chem. Sci. 1: 581; (2010)). Non-modified, natural tunicamycins are produced commercially via fermentation, usually by the commercial strain *S. chartreusis* NRRL B-3882 or *S. lysosuperificus* ATCC 31396. Tunicamycin structures are highly unusual but well characterized (Lee, et al. (2016); Campbell, et al. (2011); Li and Yu, *Angewandte Chem.* 54:6618-6621 (2015); Navarre and Schneewind (1999)); and are composed of uracil, N-acetylglucosamine (GlcNAc), an amide-linked fatty acid, and a unique 11-carbon 2-aminodialdose sugar called tunicamine Naturally-occurring tunicamycin exists as a mixture of ten or more individual components with different N-linked acyl chains (Campbell, et al. (2011)), and several structurally related compounds also exist. Mycospocidins (from *S. bobiliae*) (Neuhaus and Baddiley, *Microbiol. Mol. Biol. Rev.* 67:686-723 (2003)), streptovirudins (*S. griseoflavus* subsp. *thuringiensis*) (Brown, et al., *Chem. Biol.* 15:12-21 (2008); Soldo, et al., *Microbiology* 148:2079-2087 (2002)), antibiotics MM 19290, (*S. clavuligerus* NRRL B-3585) and 24010 (from an unidentified streptomycete) (Swoboda, et al., *Chem Bio Chem* 11:35-45 (2010); Campbell, et al., *ACS Chem. Biol.* 6, 106-116 (2011)), and corynetoxins (*Clavibacter toxicus*, also called *Corynebacterium rathayi*) (Brown, et al., *Proc. Natl. Acad. Sci. U.S.A.* 109:18909-18914 (2012)) are structurally akin to the tunicamycins, differing only in the N-acyl moiety and/or substitution of 5,6-dihydrouracil for the uracil group. More recently, a new group of related compounds was identified, and called quinovosamycins, from *S. niger* NRRL B-3857 that are identical to the tunicamycins except that the α-1"-GlcNAc headgroup is replaced by α-1"-QuiNAc (Price, et al., *J. Antibiotics* 69:637-46 (2016)). Price, et al. (2016) also identified new bacterial strains that contain the Tun biosynthetic operon that confers the ability to produce tunicamycins. Using the tunB and tunD biosynthetic gene sequences as probes of an actinomycetes genomic library, seven microorganisms with the potential for tunicamycin biosynthesis were identified, four of which are previously unreported. These strains are *Streptomyces* sp. NRRL F-4474, *S. niger* NRRL B-3857 (formally *Chainia nigra*), *Streptomyces* sp. PCS3-D2, and *Nocardia nova* SH22a, a bacterium capable of degrading gutta-percha. Other strains reported to produce tunicamycins are *S. lysosuperificus* ATCC 31396 (Takatsuki, et al. (1971)), *S. chartreusis* NRRL B-12338 and *S. chartreusis* NRRL B-3882 (Doroghazi, et al., *J. Bacteriol.* 193: 7021-2 (2011)), *Clavibacter michiganensis* ssp. *Michiganensis* (Holtmark, et al., *J. Appl. Microbiol.* 102:416-23 (2007)), and *S. torulosus* T-4 (Atta, H. M., *J. Saudi Chem. Soc.* 19:12-22 (2015)).

Because bacteria are becoming resistant to antibiotics currently on the market, a need exists for new antibiotics that are effective. Because naturally-produced tunicamycin is toxic to prokaryotes and eukaryotes, it cannot be used as an antibiotic. However, modifying tunicamycin to be non-toxic against eukaryotic cells but retain toxicity against prokaryotic cells will result in compounds that are extremely valuable antibiotic for use in animals, including humans.

BRIEF SUMMARY OF THE INVENTION

It is an object of this invention to have tunicamycin related compounds of Formula 1 and/or Formula 2 (infra) which have one reduced double bond or two reduced double bonds, respectively. It is another object of this invention to have antibacterial compositions containing one or more of these tunicamycin related compounds, alone, or in combination with one or more β-lactam antibiotics, and/or other types of antibiotics; and optionally a carrier. It is another object of this invention to have a method of killing Gram-positive bacteria in or on an animal by administering one or more of the tunicamycin related compounds of Formula 1, Formula 2, and/or Formula 3 or administering an antibacterial composition containing one or more of the tunicamycin related compounds (with or without β-lactam and/or other antibiotics) to the animal in need of treatment to kill Gram-positive bacteria. A further object of this invention is to have a method of treating a bacterial infection in or on an animal by administering one or more of the tunicamycin related compounds of Formula 1, Formula 2, and/or Formula 3, or administering an antibacterial composition containing one or more of the tunicamycin related compounds (with or without β-lactam and/or other antibiotics) to the animal in need of treatment to kill Gram-positive bacteria. Another object of this invention is have a method of disinfecting an object or a surface by applying the tunicamycin related compounds of Formula 1, Formula 2, and/or Formula 3, alone or in combination with a carrier and other components, to an object or surface to kill Gram-positive bacteria that are present on the object or surface and/or to prevent the growth of Gram-positive bacteria on the surface and/or object. It is an object of this invention to have a method of producing the tunicamycin related compounds of Formula 1, Formula 2, and/or Formula 3.

DETAILED DESCRIPTION OF THE INVENTION

Figure 1A:
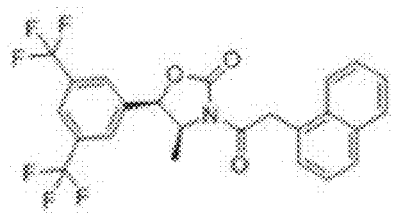
FIG. 1A shows the chemical structure of prior art tarocin A.
Figure 1B:
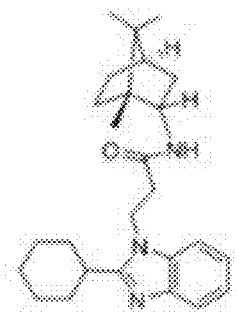
FIG. 1B shows the chemical structure of prior art tarocin B.

The present invention involves the identification, synthesis, and use of tunicamycin related compounds (novel chemical entities) that have greatly reduced or no toxicity against eukaryotic cells and animals (including human), but that are toxic against Gram-positive bacteria. These tunicamycin related compounds increase the anti-bacterial efficacy of the known β-lactam antibiotics, and thus, antibacterial compositions containing one or more tunicamycin related compounds and one or more β-lactam antibiotics are included in this invention. Also included in this invention are methods of using these tunicamycin related compounds alone or in combination with β-lactam antibiotics or other antibiotics to kill bacteria. The method of treating or preventing a bacterial disease by administering one or more of these tunicamycin related compounds, alone or in combination with β-lactam antibiotics and/or other antibiotics, are also included in this invention. Importantly, the tunicamycin related compounds can be combined with β-lactam antibiotic(s) and kill penicillin-resistant bacteria. Methods of making these tunicamycin related compounds are also covered.

One set of tunicamycin related compounds of this invention (Tun-R1) are single reduced tunicamycins in which the fatty acid acyl 2''',3'''-double bond is reduced and has the general structure of Formula 1, Formula 1

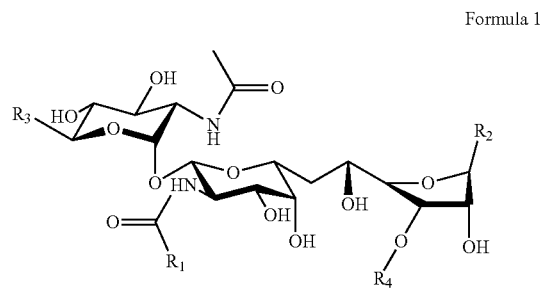

where $R_2$ is X

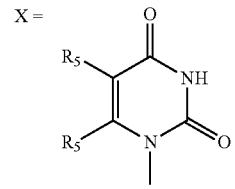

where $R_1$ is independently (i) $(CH_3)_2$—CH—$(CH_2)_n$—$CH_2$—$CH_2$— and n is independently any integer from 7 to 13, (ii) $CH_3$—$(CH_2)_n$—$CH_2$—$CH_2$— and n is independently any integer from 9 to 15, or (iii) $CH_3$—$CH_2$—CH$(CH_3)(CH_2)_n$—$CH_2$—$CH_2$— and n is independently any integer from 6 to 12; where $R_2$ is X; where $R_3$ is independently $HOCH_2$— or any alkyl (generally a $C_{1-10}$ alkyl, for example, linear alkyls (e.g., methyl, ethyl, propyl, and other linear alkyls) or branched alkyls (e.g., isopropyl, butyl, and other branched alkyls)) or other $C_{1-10}$ hydrocarbons; where $R_4$ is independently H or P—(O)(OH)$_2$; and where $R_5$ is independently H, F, Cl, Br, I, or any alkyl (generally a $C_{1-10}$ alkyl, for example, linear alkyls (e.g., methyl, ethyl, propyl, and other linear alkyls) or branched alkyls (e.g., isopropyl, butyl, and other branched alkyls)) or other $C_{1-10}$ hydrocarbons. In Tun-R1 compounds, for example, one $R_5$ can be H and the other $R_5$ can be F; one $R_5$ can be Cl and the other $R_5$ can be an ethyl group, one $R_5$ can be a methyl group and the other $R_5$ can be an ethyl group, etc. Tun-R1 compounds exclude any previously known tunicamycin compound having a fully reduced fatty acid acyl chain, e.g., the compound(s) of Formula 1 where (a) $R_2$ is X, $R_3$ is $HOCH_2$—, $R_4$ is H, $R_5$ is H, and $R_1$ is $(CH_3)_2$—CH—$(CH_2)_n$—$CH_2$—$CH_2$— then n is independently 9, 10, or 12; and (b) $R_2$ is X; $R_3$ is $HOCH_2$—; $R_4$ is H; $R_5$ is H and $R_1$ is $CH_3$—$CH_2$—$CH(CH_3)(CH_2)_n$—$CH_2$—$CH_2$— then n is independently 8, 10, or 12. See FIG. 4A for an example for one Tun-R1 structure.

The other set of tunicamycin related compounds of this invention are double reduced tunicamycins (Tun-R2) in which the fatty acid acyl 2''',3'''-double bond and the uracil 5,6-double bond are reduced and which has the general structure of Formula 2,

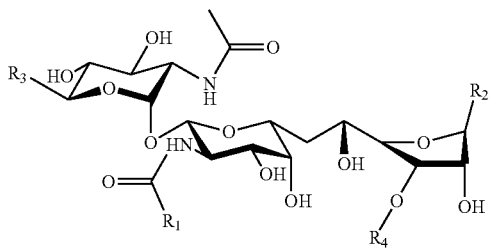

Formula 2 where $R_2$ is Y

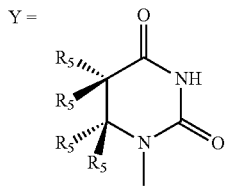

where $R_1$ is independently (i) $(CH_3)_2$—CH—$(CH_2)_n$—$CH_2$—$CH_2$— and n is independently any integer from 7 to 13, (ii) $CH_3$—$(CH_2)_n$—$CH_2$—$CH_2$— and n is independently any integer from 9 to 15, or (iii) $CH_3$—$CH_2$—CH$(CH_3)(CH_2)_n$—$CH_2$—$CH_2$— and n is independently any integer from 6 to 12; where $R_2$ is Y; where $R_3$ is independently $HOCH_2$— or any alkyl (generally a $C_{1-10}$ alkyl, for example, linear alkyls (e.g., methyl, ethyl, propyl, and other linear alkyls) or branched alkyls (e.g., isopropyl, butyl, and other branched alkyls)) or other $C_{1-10}$ hydrocarbons; where $R_4$ is independently H or P—(O)(OH)$_2$; and where $R_5$ is independently H, F, Cl, Br, I, or any alkyl (generally a $C_{1-10}$ alkyl, for example, linear alkyls (e.g., methyl, ethyl, propyl, and other linear alkyls) or branched alkyls (e.g., isopropyl, butyl, and other branched alkyls)) or other $C_{1-10}$ hydrocarbons. See FIG. 4B for an example of one Tun-R2 structure. In Tun-R2 compounds, for example, two $R_5$ can be H, a third $R_5$ can be F, and a fourth $R_5$ can be Cl; one $R_5$ can be H, two $R_5$ can be Cl and the fourth $R_5$ can be an ethyl group; one $R_5$ can be a methyl group, a second $R_5$ can be an ethyl group, a third $R_5$ can be a F, and the fourth $R_5$ can be a I; etc. Tun-R2 compounds exclude any previously known tunicamycin compound having a fully reduced fatty acid acyl chain and a fully reduced uracil ring.

Another set of tunicamycin related compounds, streptovirudins (Tun-R3), are toxic to Gram-positive bacteria and increase the anti-bacterial efficacy of the known β-lactam antibiotics. These compounds have a double-bond in the fatty acid chain but have fully reduced uracil ring and have Formula 3.

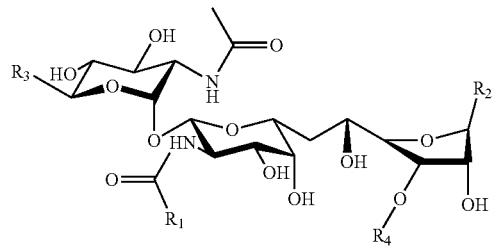

Formula 3 where $R_2$ is Y

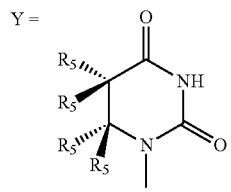

where $R_1$ is independently (i) $(CH_3)_2$—CH—$(CH_2)_n$—$CH_2$=$CH_2$— and n is independently any integer from 6 to 8 or, (ii) $CH_3$—$CH_2$—$CH(CH_3)(CH_2)_n$—$CH_2$=$CH_2$— and n is independently any integer from 6 to 8; where $R_2$ is Y; where $R_3$ is independently $HOCH_2$— or any alkyl (generally a $C_{1-10}$ alkyl, for example, linear alkyls (e.g., methyl, ethyl, propyl, and other linear alkyls) or branched alkyls (e.g., isopropyl, butyl, and other branched alkyls)) or other $C_{1-10}$ hydrocarbons; where $R_4$ is independently H or P—(O)(OH)$_2$; and where $R_5$ is independently H, F, Cl, Br, I, or any alkyl (generally a $C_{1-10}$ alkyl, for example, linear alkyls (e.g., methyl, ethyl, propyl, and other linear alkyls) or branched alkyls (e.g., isopropyl, butyl, and other branched alkyls)) or other $C_{1-10}$ hydrocarbons. See FIG. 4C for the structure of one of the Tun-R3 compounds.

As used herein, the term "tunicamycin related compound(s)" is one or more tunicamycin, quinovosamycin, and/or streptovirudin which has undergone a chemical reaction to reduce the fatty acid acyl 2''',3'''-double bond and/or the uracil 5,6-double bond. Also, the naturally occurring streptovirudin compounds of Formula 3 are included in the definition of tunicamycin related compounds. The terms "modified tunicamycin(s)", "tunicamycin compound(s) derivative", "tunicamycin-related compound(s)", and similar names have the same meaning. The term "Tun-R1" refers to a tunicamycin related compound that has undergone a chemical reaction to reduce the fatty acid acyl 2''',3'''-double bond only. The term "Tun-R2" refers to a tunicamycin related compound that has undergone a chemical reaction to reduce the fatty acid acyl 2''',3'''-double bond and the uracil 5,6-double bond. The term "Tun-R3" refers to the streptovirudin compounds of Formula 3. The term "unmodified tunicamycin(s)" are tunicamycin(s) that have not yet undergone reduction of a double bond in the uracil ring, or in both the uracil ring and the fatty acid acyl chain.

Gram-positive bacteria are bacteria that appear violet or purple after exposure to the Gram stain test. Gram-positive bacteria contains a peptidoglycan layer in the cell wall; the Gram stain binds to or is absorbed by this peptidoglycan layer such that the stain remains after a wash. Non-limiting examples of Gram-positive bacteria include *Actinomyces* sp., *Bacillus* sp., *Clavibacter* sp., *Clostridium* sp., *Coryne-*

*bacterium* sp., *Enterococcus* sp., *Lactobacillus* sp., *Leifsonia* sp., *Listeria* sp., *Mycobacterium* sp., *Mycoplasma* sp., *Nocardia* sp., *Propionibacterium* sp., *Rathybacter* sp., *Staphylococcus* sp., *Streptococcus* sp., and *Streptomyces* sp. *Bacillus subtilis* strain MW10 is commonly used in experiments as an example for Gram-positive bacteria. *Escherichia coli* is commonly used in experiments as an example for Gram-negative bacteria.

As mentioned supra, certain *Streptomyces* species naturally produce tunicamycin and streptovirudin. These species of Streptomyces produce these compounds with fatty acid acyl chains of varying lengths. In one embodiment of this invention, when discussing Tun-R1 (Formula 1), Tun-R2 (Formula 2), and Tun-R3 (Formula 3) compounds, each (Tun-R1, or Tun-R2, or Tun-R3, as indicated by the language) are a mixture of compounds with varying lengths of fatty acid acyl chains. In another embodiment, the particular tunicamycin related compound has a fatty acid acyl chain of the indicated length. In addition, the Streptomyces species produce naturally-occurring tunicamycins and naturally-occurring streptovirudin containing a trans 2''',3'''-double bond in the fatty acid acyl chain. As such, the naturally-occurring Tun-R3 compounds contain a trans 2''',3'''-double bond in the fatty acid acyl chain. However, one could chemically synthesize Tun-R3 compounds containing a racemic mixture of cis and trans 2''',3'''-double bond in the fatty acid acyl chain or containing only cis 2''',3'''-double bond in the fatty acid acyl chain, or containing only trans 2''',3'''-double bond in the fatty acid acyl chain.

The method of making Tun-R1 compounds from unmodified tunicamycins is part of this invention. The most common approach to reduce double bonds is direct hydrogenation using an external source of hydrogen gas in the presence of a metal catalyst. Catalytic hydrogenation of double bonds is reviewed in Vollharde and Schore, *Organic Chemistry: Structure and Function*. New York: W.H. Freeman and Company, 2007. In one embodiment, hydrogenation of double bonds is achieved with hydrogen gas at atmospheric pressure (1 hour, 25° C.) using 10% Pd-on-carbon catalyst in MeOH (Price, et al, *Carbohydrate Res.* 289:115-136 (1996)). Alternatively, catalytic transfer hydrogen methods that utilize an additional reagent to generate hydrogen in-situ can be used. Thus, in one embodiment, to reduce the acyl double bond, the unmodified tunicamycin(s) is placed in an acidic (pH ranging from approximately pH 1 to approximately pH 5, or approximately pH 3 to approximately pH 5), organic liquid (solvent). Non-limiting examples of an organic liquid (solvent) are DMSO, methanol, ethanol, any other alcohol, toluene, DMF, THF, chloroform, and combinations thereof. To lower the pH of the organic liquid, one combines an acid with the organic liquid. Non-limiting examples of useful acids are acetic acid, boric acid, propionic acid, citric acid, succinic acid, and formic acid, or any other mild acid in an amount sufficient to maintain the desired pH range. A strong acid can be diluted to become a mild acid. In another embodiment, instead of adding an acid to the organic liquid, one adds a cation exchange resin to the organic liquid to lower the pH of the organic liquid. Non-limiting examples of a cation exchange resin include sulfonic based cation exchange resin and carboxylic based cation exchange resin. A sufficient amount of palladium on carbon catalyst (3% palladium on carbon, 5% palladium on carbon, 10% palladium on carbon), or any other metal supported on carbon catalyst (e.g., rhodium on carbon), or other metal catalysts (e.g., nickel, indium, and Raney nickel) is added and then sufficient amount (a slight molar excess) of sodium borohydride or other agents that hydrogenate a double-bond to a single bond (e.g., cyanoborohydride, lithium aluminum hydride ($LiAlH_4$), triethylsilane ($Et_3SiH$), sodium cyanoborohydride, and lithium triethylborohydride) is added. A "sufficient amount" of the catalyst is that amount which is slightly more than necessary to drive the reaction to completion, i.e., to generate sufficient hydrogen to fully reduce the fatty acid acyl chain double bond. A "sufficient amount" of the agent that hydrogenates double bonds is that amount which is slightly more than amount necessary to fully reduce the fatty acid acyl chain double bond, and which is a slight molar excess. The reaction is stirred until all of the unmodified tunicamycins' acyl double bonds are reduced. In one embodiment, the reaction temperature is approximately room temperature. In other embodiments, the reaction temperature can range from approximately 10° C. to approximately 35° C. Depending on the temperature of the reaction, that time period can range from approximately 5 minutes to approximately 3 hours; alternatively from approximately 10 minutes to approximately 2 hours; or alternatively from approximately 15 minutes to approximately 1 hour. Removal of the catalyst is performed by filtration or other known in the art methods for separating a catalyst from the compounds such as centrifugation. The filtrate is dried and resuspended in an alcohol which is heated to convert the residual sodium borohydride and the acid to volatile organics which are removed by evaporation. In one embodiment, the alcohol is methanol but ethanol, butanol, etc., can be used. The amount of time and temperature can vary for conversation of sodium borohydride and the acid to volatile organics. The residue are Tun-R1 compounds.

The method of making Tun-R2 compounds from tunicamycins is part of this invention. The most common approach to reduce double bonds is direct hydrogenation using hydrogen gas in the presence of a metal catalyst. See, Vollharde and Schore, *Organic Chemistry: Structure and Function*. New York: W.H. Freeman and Company, 2007, for various protocols. In one embodiment, hydrogenation of double bonds is achieved with hydrogen gas at atmospheric pressure (1 hour, 25° C.) using 10% Pd-on-carbon catalyst in MeOH (Price, et al (1996)). Alternatively, catalytic transfer hydrogen methods that utilize an additional reagent to generate hydrogen in-situ can be used. Thus, in one embodiment, unmodified tunicamycin(s) is placed in an acidic (pH ranging from approximately pH 1 to approximately pH 5, or approximately pH 3 to approximately pH 5), organic liquid (solvent). Non-limiting examples of an organic liquid (solvent) are DMSO, methanol, ethanol, any other alcohol, toluene, DMF, THF, chloroform, and combinations thereof. To lower the pH of the organic liquid, one combines an acid with the organic liquid. Non-limiting examples of useful acids are acetic acid, propionic acid, boric acid, citric acid, succinic acid, and formic acid, or any other mild acid in sufficient amount to maintain the desired pH range. A strong acid can be diluted to become a mild acid. In another embodiment, instead of adding an acid to the organic liquid, one adds a cation exchange resin to an organic liquid to lower the pH of the organic liquid. Non-limiting examples of a cation exchange resin include sulfonic based cation exchange resin and carboxylic based cation exchange resin. A sufficient amount of palladium on carbon catalyst (3% palladium on carbon, 5% palladium on carbon, 10% palladium on carbon), or any other metal supported on carbon catalyst (e.g., nickel, indium, and rhodium on carbon), or other metal catalysts (e.g., Raney nickel) is added and then sufficient amount (a slight molar excess) of sodium borohydride ($NaBH_4$) or other agents that hydrogenate two double-bonds to a single bonds (e.g., cyanoborohydride, lithium aluminum hydride (LiAlH$_4$), triethylsilane (Et$_3$SiH), sodium cyanoborohydride, and lithium triethylborohydride) is added. A "sufficient amount" of the catalyst is that amount which is slightly more than necessary to drive the reaction to completion, i.e., to generate sufficient hydrogen to fully reduce the fatty acid acyl chain double bond and the uracil ring double bond. A "sufficient amount" of the agent that hydrogenates double bonds is that amount which is slightly more than amount necessary to fully reduce the fatty acid acyl chain double bond and the uracil ring double bond, and which is a slight molar excess. The reaction is stirred for approximately 20 hours to approximately 80 hours, depending on the reaction's temperature which can range from approximately 50° C. to approximately 90° C.; the higher temperature causing a quicker reaction. In one embodiment, reaction time is approximately 40 hours to approximately 60 hours and reaction temperature is between approximately 55° C. to approximately 70° C. The reaction continues until both double bonds in all of the tunicamycins are reduced. The reaction is allowed to cool to room temperature and then the catalyst is remove, for example, by filtration or centrifugation or other separation techniques known in the art. The filtrate is dried and resuspended in an alcohol which is heated to convert the residual sodium borohydride and the acid to volatile organics which are removed by evaporation. In one embodiment, the alcohol is methanol but ethanol, butanol, etc., can be used. The amount of time and temperature can vary for conversation of sodium borohydride and the acid to volatile organics. The residue are Tun-R2 compounds.

The tunicamycin related compounds of this invention can be combined with penicillin and/or other antibiotics in the penicillin family. The combination product has synergist effect of enhancing toxicity against bacteria (Gram-positive bacteria), thereby allowing less penicillin or its related antibiotics being used to kill the bacteria. The combination product can overcome the resistance to penicillin that many bacteria have developed. Non-limiting examples of penicillin antibiotics include naturally occurring penicillins (penicillin G and penicillin V), β-lactamase resistant penicillins (methicillin, nafcillin, oxacillin, cloxacillin, dicloxacillin), aminopenicillins (ampicillin, amoxicillin, pivampicillin, hetacillin, bacampicillin, metampicillin, talampicillin, epicillin), carboxypenicillins (carbenicillin, ticarcillin) and ureidopenicillins (mezlocillin, piperacillin). Other penicillians include azlocillin and flucloxacillin.

Penicillins are β-lactam antibiotics. So, the tunicamycin related compounds can be combined with any β-lactam antibiotics and have enhanced antibacterial activity. In addition to penicillins, β-lactam antibiotics include, but are not limited to cephalosporins, monobactams (such as, aztreonam, tigemonam, nocardicin A, and tabtoxin) and carbapenems (such as, imipenem/cilastatin, meropenem, ertapenem, doripenem, panipenem, biapenem, razupenem, tebipenem, lenapenem, tomopenem, and thienamycin). Non-limiting examples of cephalosporins includes cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefuroxime, cefuzonam, cefmetazole, cefotetan, cefoxitin, cefbuperazone, cefminox, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxoxime, ceftriaxone, cefoperazone, ceftazidime, oxacephems (including latamoxef and flomoxef), cefclidine, cefepime, cefluprenam, cefoselis, cefozopran, cefpirome, cefquinome, ceftobiprole, ceftaroline, and ceftolozane.

The tunicamycin related compounds can be combined with antibiotics that are not β-lactam antibiotics (referred to herein as "non-β-lactam antibiotic"), including but not limited to geldanamycin, herbimycin, carbacephem, loracarbef, cefalothin, cefalexin, cefamandole, cefoxitin, cefprozil, teicoplanin, vancomycin, macrolides, azithromycin, clarithromycin, dirithromycin, erythromycin, roxithromycin, troleandomycin, telithromycin, spectinomycin, aztreonam, bacitracin, colistin, polymyxin B, quinolones, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole (TMP-SMX), demeclocycline, doxycycline, minocycline, oxytetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin or rifampicin, and/or tinidazole; to name a few. Other antibiotics known in the art that are used against Gram-positive bacteria may be added to the compositions described herein, provided they do not substantially interfere with the intended activity and efficacy of the compositions described herein. Whether or not another antibiotic interferes with activity and/or efficacy of the compositions described herein can be determined, for example, by the procedures utilized below.

As used herein "in amounts effective" or "an effective amount" refer to the amount of tunicamycin related compounds or antibacterial compositions containing the tunicamycin related compounds (with or without other antibiotics) that, when it is administered to or on an animal, kills bacteria that live in or on the animal. Applying/administering an effective amount of the tunicamycin related compounds or antibacterial compositions containing the tunicamycin related compounds to an animal is the application/administering of that amount which is necessary to kill bacteria, prevent the growth of bacteria, to prevent a bacterial disease, to treat a bacterial disease in or on the animal being treated. An effective amount of one or more tunicamycin related compounds (or compositions containing the tunicamycin related compounds) to disinfect an object or surface is that amount which, when applied to the object or surface, will kill bacteria on that object or surface and/or which will prevent the growth of bacteria on that object or surface.

In various embodiments, an appropriate dosage level for administration to an animal will generally be approximately 0.000001 mg per kg body weight of the animal to approximately 10 g per kg body weight of the animal per day and can be administered in single or multiple doses. In one embodiment, the dosage level can be approximately 0.01 mg/kg/day to approximately 1 g/kg/day; in another embodiment approximately 0.1 mg/kg/day to approximately 500 mg/kg/day. In another embodiment, a suitable dosage level can be approximately 0.01 mg/kg/day to approximately 250 mg/kg/day; or alternatively approximately 0.05 mg/kg/day to approximately 100 mg/kg/day; or alternatively approximately 0.1 mg/kg/day to approximately 50 mg/kg/day. In other embodiments, the dosage can be approximately 0.05 mg/kg/day to approximately 0.5 mg/kg/day; approximately 0.5 mg/kg/day to approximately 5.0 mg/kg/day; or approximately 5.0 mg/kg/day to approximately 50 mg/kg/day. The compound can be administered on a regimen of approximately 1 to approximately 4 times per day, or alternatively approximately once or approximately twice per day. This dosing regimen can be adjusted to provide the optimal therapeutic response. In another embodiment, one or more tunicamycin related compounds are combined with a β-lactam antibiotic in an antibacterial composition. In such antibacterial compositions, the amount of the β-lactam antibiotic can range from approximately 0.002 µg/ml to approximately 10 µg/ml and the amount of the tunicamycin related compounds can range from approximately 0.002 µg/ml to approximately 10 µg/ml.

Exemplary administration of tunicamycin related compounds or antibacterial compositions containing the tunicamycin related compounds can be a relatively short-term period lasting approximately one or approximately two days, approximately one or approximately two weeks, or approximately one, approximately two or even approximately three months. Exemplary administration of tunicamycin related compounds or antibacterial compositions containing the tunicamycin related compounds can be a relatively long-term period lasting from approximately three or approximately four months to approximately one year, or even longer. Exemplary routes of administration of the tunicamycin related compounds and antibacterial compositions containing tunicamycin related compounds of this invention include, but are not limited to, intramuscular injection, intraperitoneal injection, subdermal injection, intradermal injection, subcutaneous injection, intravenous injection, oral administration, sublingual administration, vaginal administration, rectal administration, transmucosally, transcutaneous adsorption, intranodal administration, intracoronary administration, intraarterial administration, intratracheal administration, intraarticular administration, intraventricular administration, intracranial administration, intraspinal administration, intraocular administration, aural administration, inhalation, eye drop administration, and intranasal administration. In another embodiment, the tunicamycin related compounds or antibacterial compositions containing the tunicamycin related compounds may be mixed with an animal's feed or water.

In yet another embodiment, the tunicamycin related compounds or antibacterial compositions containing the tunicamycin related compounds may be further formulated with a carrier (pharmaceutically or veterinarianly acceptable carrier) to facilitate administration. The carrier can take a wide variety of forms depending on the form of preparation desired for administration, e.g., oral or parenteral (including intravenous), or application, e.g., applied topically or on the surface. The tunicamycin related compounds or antibacterial compositions containing the tunicamycin related compounds can be presented as discrete units suitable for oral administration, such as capsules, cachets or tablets, lozenges, dissolvable strips, etc., each containing a predetermined amount of the tunicamycin related compounds or antibacterial compositions containing the tunicamycin related compounds. Further, the tunicamycin related compounds or antibacterial compositions containing the tunicamycin related compounds can be presented as a powder, as a cream, as an ointment, as granules, as a solution, as a suspension in an aqueous liquid, as a non-aqueous liquid, as an oil-in-water emulsion or as a water-in-oil liquid emulsion. In addition to the common dosage forms set out above, the tunicamycin related compounds or antibacterial compositions containing the tunicamycin related compounds can also be administered by controlled release devices and/or delivery devices.

The tunicamycin related compounds can be prepared by any of the methods described herein or any other method known to one of skill in the art. Compositions containing the tunicamycin related compounds can then be made using such methods that include a step of bringing into association the tunicamycin related compounds or antibacterial compositions containing the tunicamycin related compounds with the carrier. In general, the compositions are prepared by uniformly and intimately admixing the tunicamycin related compounds or antibacterial compositions containing the tunicamycin related compounds with liquid carriers or finely divided solid carriers or both. The product can then be conveniently shaped into the desired presentation.

In preparing the active agents for oral dosage form, any convenient pharmaceutical or veterinarian carriers can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Optionally, tablets can be coated by standard aqueous or non-aqueous techniques. Non-limited examples of carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, stearic acid, magnesium, and mineral oils. Suitable carriers and formulations are described in detail in *Remington's Pharmaceutical Sciences* (19th ed., 1995).

The tunicamycin related compounds or antibacterial compositions containing the tunicamycin related compounds suitable for parenteral administration can be prepared as solutions or suspensions or emulsions or dispersions in water or other liquid. A suitable surfactant can be included; such as, for example, hydroxypropylcellulose. The tunicamycin related compounds or antibacterial compositions containing the tunicamycin related compounds can also be prepared in glycerol, liquid polyethylene glycols, and mixtures thereof in oils. Further, a preservative can be included to prevent the detrimental growth of eukaryotic microorganisms.

If applicable, a tablet containing the tunicamycin related compounds or antibacterial compositions containing the tunicamycin related compounds can be prepared by compression or molding, optionally with one or more accessory ingredients or adjuvants. Compressed tablets can be prepared by compressing, in a suitable machine, the active agents of the invention in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Compositions of the present invention suitable for injectable use include sterile aqueous solutions, emulsions, or dispersions. Furthermore, the compositions can be in the form of sterile powders for the extemporaneous preparation of such sterile injectable solutions, emulsions, or dispersions. In all cases, the final injectable form must be sterile and must be effectively fluid for easy syringability. The pharmaceutical compositions must be stable under the conditions of manufacture and storage; thus, preferably should be preserved against the contaminating action of eukaryotic microorganisms. The carrier can be a solvent or dispersion medium containing, for example, water, ethanol, polyol (e.g., glycerol, propylene glycol and liquid polyethylene glycol), vegetable oils, and suitable mixtures thereof.

Compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing the compound(s) of the invention via conventional processing methods. As an example, a cream or ointment is prepared by mixing hydrophilic material and water, together with about 5 wt % to about 10 wt % of the active agent(s) to produce a cream or ointment having a desired consistency.

As a disinfectant, the tunicamycin related compounds or antibacterial compositions containing the tunicamycin related compounds can be made into a solution, suspension, emulsion, gel, or spray that can be wiped on, sprayed on, poured on, etc., onto a surface. It also can be a solution, suspension, or gel into which a body part or object is dipped. It can also be made into a solution, suspension, emulsion, gel, or similar type of compound that can be applied to an object or animal or part of an animal. Such disinfecting solutions, suspensions, emulsions, gels, or sprays containing one or more the tunicamycin related compounds can be applied to medical or veterinarian instruments, especially those for which are sensitive to extreme heat and/or pressure and thus would be damaged by autoclaving. In such disinfectant solutions, suspensions, emulsions, gels, or sprays, the amount of each tunicamycin related compound can range between approximately 0.001 µg/ml to approximately 1 g/ml in one embodiment, between approximately 0.01 µg/ml to approximately 100 mg/ml in another embodiment, between approximately 0.1 µg/ml to approximately 10 mg/ml in another embodiment, or between approximately 1 µg/ml to approximately 1 mg/ml in another embodiment.

One type of disinfectant solution or suspension can be a mouthwash. Such a mouthwash may have one or more of the following ingredients water, phenol, thymol, eugenol, eucalyptol, menthol, alcohol, chlorhexidine gluconate, cetylpyridinium chloride, hexetidine, benzoic acid, methyl salicylate, triclosan, benzalkonium chloride, methylparaben, hydrogen peroxide, domiphen bromide and/or fluoride. Some mouthwashes also include sweeteners, such as sorbitol, sucralose, sodium saccharin, and xylitol. The amount of the tunicamycin related compounds can range from between approximately 0.001 µg/ml to approximately 1 g/ml in one embodiment, between approximately 0.01 µg/ml to approximately 100 mg/ml in another embodiment, between approximately 0.1 µg/ml to approximately 10 mg/ml in another embodiment, or between approximately 1 µg/ml to approximately 1 mg/ml in another embodiment.

In addition to the aforementioned carrier ingredients, the formulations described above can include, as appropriate, one or more additional carrier ingredients such as diluents, buffers, flavoring agents, binders, surface-active agents, thickeners, lubricants, preservatives (including anti-oxidants) and the like. Furthermore, compounds can be included to render the formulation isotonic with the blood of the intended recipient. Compositions containing the compound(s) of the invention can also be prepared in powder or liquid concentrate form.

Thus, another embodiment of this invention is the method of disinfecting a surface or object by applying at least tunicamycin related compound, or a composition containing at least one tunicamycin related compound, to that surface or object to kill any Gram-positive bacteria that are present on the surface or object; and/or keep Gram-positive bacteria from growing on that surface or object. As discussed supra, the object can be, but are not limited to, a medical device, kitchen appliance, tool, equipment in general, soil, and an animal's skin, fur, hair, teeth or other body part. A surface can be, but is not limited to, a counter-top, a table-top, and any other item for which one wants to stop bacteria on it.

This invention described herein may be administered to canine, feline, bovine, swine, equine, ovine, goats, camels, and any other mammal including humans; birds (including but not limited to chickens, turkeys, quail, ducks, and other domesticated birds); amphibians; reptiles; and fish.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The terms "approximately" and "about" refers to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria. The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range. "Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent. The invention illustratively disclosed herein suitably may be practiced in the absence of any element which is not specifically disclosed herein.

Tunicamycin Pharmacodynamics

The teichoic acids are a group of polyanionic polymers found only as a cell surface component of Gram-positive bacteria, and are implicated in anchoring proteins to the bacterial surface (Navarre and Schneewind, *Microbiol. Mol. Biol. Rev.* 63:174-229 (1999)), modulating enzymes involved in autolysis (Calamita & Doyle, *Mol. Microbiol.* 44(3):601-6 (2002); Schlag, et al., *Mol. Microbiol.* 75(4): 864-73 (2010)).

Figure 2:
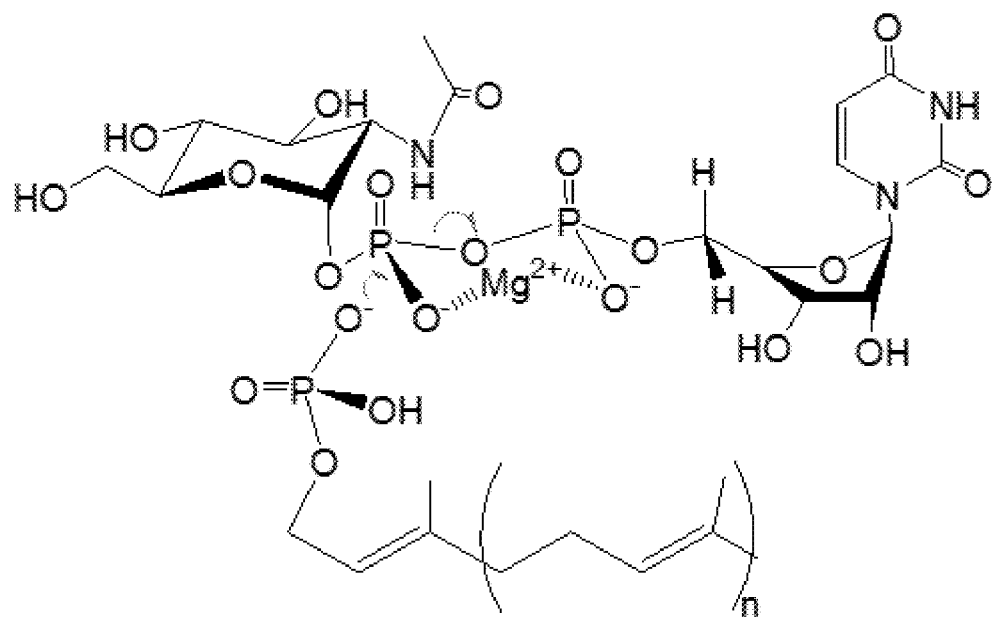
FIG. 2 shows the transition state for UDP-N-acetyl-D-glucosamine: polyprenol-phosphate N-acetylglucosamine-1-phosphate translocases, target enzymes for inhibition by tunicamycins.

TagO is a bacterial membrane protein, and a member of the UDP-N-acetyl-D-hexosamine: polyprenol-phosphate N-acetylhexosamine-1-phosphate translocases, a family of enzymes involved in bacterial cell wall synthesis and eukaryotic protein N-glycosylation (Lee, et al. (2016); Navarre and Schneewind (1999)). Tunicamycin is a potent inhibitor of bacterial TagO/WecA (UDP-N-acetylglucosamine-type translocases) and MraY (UDP-N-acetylmuramate-pentapeptide-type translocase), respectively blocking the initial steps for both teichoic acid (in Gram-positive bacteria) and peptidoglycan biosynthesis (in all bacteria). In eukaryotes, including mammals, the target translocase known as GPT (UDP-GlcNAc: dolichol-P GlcNAc-1-P transferase) catalyzes the biosynthesis of N-acetylglucosamine-linked dolichol pyrophosphate, an early event in protein N-glycosylation. As such, tunicamycin is widely used to inhibit glycoprotein translocation and processing. Not wishing to be bound to any particular hypothesis, the translocase reaction most probably occurs by a unimolecular nucleophilic substitution involving a transient N-acetylhexosaminyl phosphonium ionic intermediate, or by a direct $S_N2$ attack of the polyprenol phosphate on the α-phosphate of the uridyl diphosphate N-acetylhexosamine (UDP-GlcNAc, FIG. 2). As a structural mimic of the transition state, the N-acylated tunicamine-uracil moiety is presumed to be an analog of the polyprenol-pyrophosphate and uridyl groups, whereas the α-1", β11'-linked GlcNAc residue mimics the GlcNAc group of the transition state.

Tunicamycins are hypothesized to be transition state mimics of UDP-N-acetyl-D-glucosamine: polyprenol-phosphate N-acetylglucosamine-1-phosphate translocases, such as bacterial TagO and eukaryotic GPT proteins. Note that the polyprenol phosphate acceptor substrate for bacterial TagO has an unsaturated α-terminal prenol group whereas the corresponding position in eukaryotic dolichol phosphate acceptors are saturated.

Figure 3A:
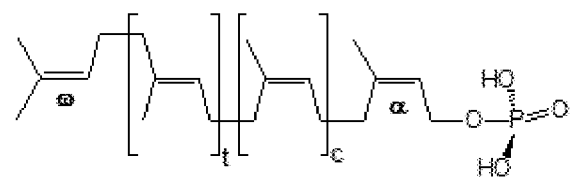
FIG. 3A shows the bacterial undecaprenol-P substrates used by the UDP-N-acetyl-D-glucosamine: polyprenol-phosphate N-acetylglucosamine-1-phosphate translocase enzymes for bacterial teichoic acid biosynthesis.
Figure 3B:
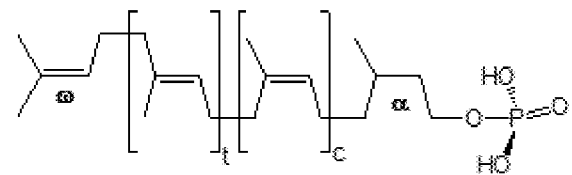
FIG. 3B shows the eukaryotic dolichol-P type polyprenol phosphate acceptor substrates used by the UDP-N-acetyl-D-glucosamine: polyprenol-phosphate N-acetylglucosamine-1-phosphate translocase enzymes for eukaryotic protein glycosylation (GPT).

Kinetic studies (Brandish, et al., *J. Biol. Chem.* 29(271): 7609-14 (1996a)) have shown that tunicamycin is a competitive inhibitor of UDP-N-acetyl-D-glucosamine: polyprenol-phosphate N-acetylglucosamine-1-phosphate translocases with respect to the UDP-GlcNAc sugar nucleotide substrate, and that it is non-competitive with regards to the polyprenol-phosphate (Brandish, et al., *Antimicrob. Agents Chemother.* 40:1640-4 (1996b)). This shows that tunicamycin competes with the UDP-GlcNAc for binding at the active site of TagO, but that the tunicamycin fatty acid chain does NOT compete with the polyprenol-phosphate binding. The current art (Brandish, et al. (1996b)) therefore teaches that the tunicamycins inhibit UDP-N-acetyl-D-hexosamine: polyprenol-phosphate N-acetylhexosamine-1-phosphate translocases irrespective of which polyprenol-phosphate is used as the acceptor substrate. For bacterial translocases (including TagO and MraY) the polyprenol-phosphate is typically undecaprenol phosphate (also called bactoprenol phosphate), a C-55 isoprenyl-based molecule in which the α-terminal prenol group is unsaturated. For the eukaryotic GPT translocates the respective polyprenol-phosphate acceptor substrate is known as dolichol phosphate, in which the α-terminal prenol group is fully saturated. FIG. 3A shows the bacterial undecaprenol-P substrates used by the UDP-N-acetyl-D-glucosamine: polyprenol-phosphate N-acetylglucosamine-1-phosphate translocase enzymes for bacterial teichoic acid biosynthesis. FIG. 3B shows the eukaryotic dolichol-P type polyprenol phosphate acceptor substrates used by the UDP-N-acetyl-D-glucosamine: polyprenol-phosphate N-acetylglucosamine-1-phosphate translocase enzymes for eukaryotic protein glycosylation (GPT). The naturally-occurring tunicamycins contain a fatty acid 2''',3'''-double bond, similar to the positioning of the double bond in the α-prenol group of undecaprenol phosphate (FIG. 3A and FIG. 3B).

Based on these observations, one would expect that natural tunicamycins, that contain a conjugated 2''',3'''-double bond in the fatty acid chain, would be a better substrate analog of the unsaturated undecaprenol phosphate of bacterial translocases, and that tunicamycin related compounds with the 2''',3'''-double bond reduced (and therefore fully saturated) would be more potent inhibitors of eukaryotic translocases. Hence unsaturated (natural) tunicamycins would be toxic to bacteria, and saturated (reductively modified) tunicamycin related compounds would be more toxic to eukaryotes than unsaturated (natural) tunicamycins.

Surprisingly and unexpectedly, the tunicamycin related compounds of this invention have the opposite effect. The chemically reduced tunicamycins are unexpectedly much less toxic to eukaryotes, but still retain their antibacterial activity and enhance the activity of β-lactams. Even more unexpectedly, the reduction of the double bond in the uracil ring of the tunicamycin related compounds result in even greater reduction in the eukaryotic toxicity, so that these doubly reduced tunicamycins are apparently non-toxic towards either yeast or cultured human breast cancer cells. Furthermore, based on the results of a SDS-PAGE-based protein glycosylation assay, the tunicamycin related compounds with the double reduction of the 2''',3'''-acyl and 5,6-uracil double bonds have lost the ability to inhibit glycoprotein synthesis, but are still able to enhance the activity of the penicillins against Gram-positive bacteria in a synergistic manner. See examples, infra.

The following examples are provided to illustrate certain particular features and/or embodiments. These examples should not be construed to limit the disclosure to the particular features or embodiments described.

EXAMPLE 1

Quantitative Structure-activity Relationship (QSAR) Study to Identify Tunicamycin Structures that have Potent Inhibitory Effects on Bacteria and have Low Toxicity in Eukaryotes The aim of this study is to determine whether certain structural features of the tunicamycins can be used to distinguish their relative biological activity on bacteria and eukaryotes. A library of chemically synthesized tunicamycins was previously published by Li and Yu (2015), but biological testing of this library has not been undertaken previously. The library of ten structurally-diverse synthetic tunicamycins (referred to as compounds 1 to 10) are obtained from Dr. Biao Yu, and are tested for their antimicrobial activity against a model Gram positive bacterium (*Bacillus subtilis*), and against a model eukaryote (*Saccharomyces cerevisiae,* bakers' yeast). Naturally-occurring tunicamycins produced by *Streptomyces chartreusis* NRRL 3882 (Sigma-Aldrich Inc., St. Louis, Mo.) are used as a positive control, and the solvent DMSO as the null control. See Table 1, infra (DMSO results are not shown). The structural validity of the compounds in the library is confirmed by matrix-assisted laser desorption/ionization-time of flight (MALDI-TOF) mass spectrometry. The synthetic tunicamycin analogs in the library are tested at equivalent concentrations for growth inhibition of the microbes using a standard agar diffusion-zone of inhibition assay. See, Bauer et al., *Am. J. Clin. Pathol.* 36:493-496 (1966). The "zone of clearing" results are provided in Table 1, infra.

TABLE 1

| ID | Name | Structure | Zone of Clearing (cm) | |
| --- | --- | --- | --- | --- |
| | | | *B. subtilis* | Yeast |
| T | Natural tunicamycin | [Structure shown; n = 8-11] | 2.5 | 2.5 |
| 1 | TB-1 | [Structure shown] Chemical Formula: $C_{23}H_{36}N_4O_{15}$; Exact Mass: 608.2177; Molecular Weight: 608.5497 | 0 | 0 |
| 2 | TB-2 | [Structure shown] Chemical Formula: $C_{38}H_{62}N_4O_{16}$; Exact Mass: 830.4161; Molecular Weight: 830.9161 | 2.5 | 2.4 |
| 3 | TB-3 | [Structure shown] Chemical Formula: $C_{38}H_{64}N_4O_{16}$; Exact Mass: 832.4317; Molecular Weight: 832.9320 | 2.3 | 0.2 |

TABLE 1-continued
| ID | Name | Structure | Zone of Clearing (cm) | |
| | | | B. subtilis | Yeast |
| --- | --- | --- | --- | --- |
| 4 | TB-4 | 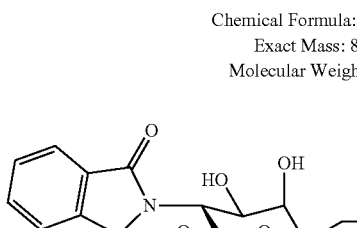 Chemical Formula: $C_{36}H_{58}N_6O_{15}$<br>Exact Mass: 814.3960<br>Molecular Weight: 814.8769 | 1.6 | 0 |
| 5 | TB-5 | 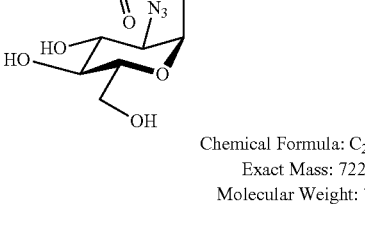 Chemical Formula: $C_{29}H_{34}N_6O_{16}$<br>Exact Mass: 722.2031<br>Molecular Weight: 722.6109 | 0 | 0 |
| 6 | TB-6 | 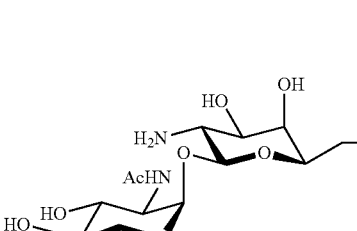 Chemical Formula: $C_{26}H_{40}N_2O_{15}$<br>Exact Mass: 620.2429<br>Molecular Weight: 620.6002 | 0 | 0 |
| 7 | TB-7 | 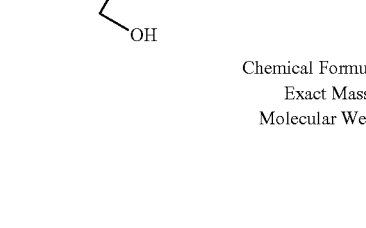 Chemical Formula: $C_{41}H_{66}N_2O_{16}$<br>Exact Mass: 842.4412<br>Molecular Weight: 842.9665 | 0 | 0 |

TABLE 1-continued

| ID | Name | Structure | Zone of Clearing (cm) B. subtilis | Yeast |
|---|---|---|---|---|
| 8 | TB-8 | 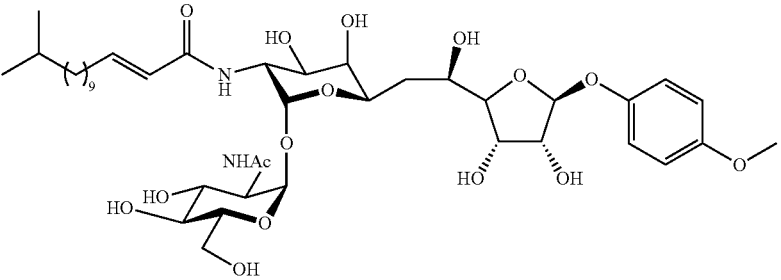 Chemical Formula: $C_{41}H_{66}N_2O_{16}$<br>Exact Mass: 842.4412<br>Molecular Weight: 842.9665 | 0 | 0 |
| 9 | TB-9 | 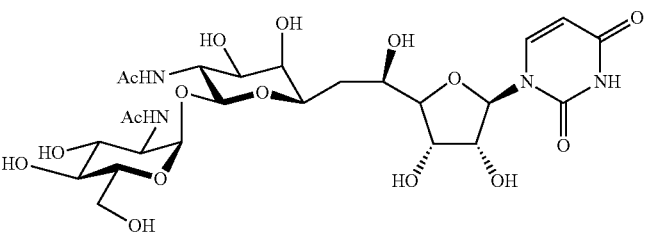 Chemical Formula: $C_{25}H_{38}N_4O_{16}$<br>Exact Mass: 650.23<br>Molecular Weight: 650.59 | 0 | 0 |
| 10 | TB-10 | 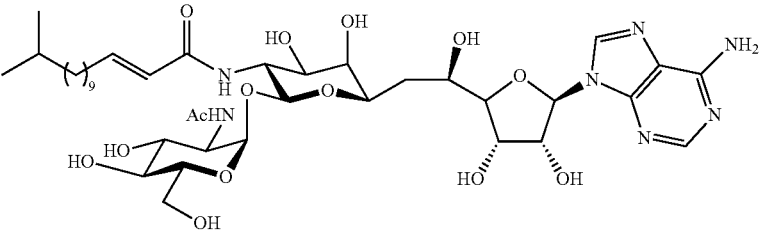 Chemical Formula: $C_{31}H_{47}N_7O_{14}$<br>Exact Mass: 741.32<br>Molecular Weight: 741.75 | 0 | 0 |

The naturally-occurring tunicamycins (positive control, T) display the expected potent toxicity (0.5 μg spotted) against *Bacillus* and *S. cerevisiae* in the agar diffusion assay, giving a zone of clearing of ~2.5 cm. Similarly, the chemically synthesized Compound 2 gives the same antimicrobial activity as the native tunicamycin against both test organisms. Both the naturally-occurring tunicamycins and Compound 2 contain the 2′″,3′″-conjugated double bond in the N-linked fatty acid chain. Compound 3 gives a comparable response on the *Bacillus*. However, unexpectedly, Compound 3, which only differs from Compound 2 in that it contains a fully saturated N-linked fatty acid chain, is considerably less toxic against *S. cerevisiae* compared to naturally-occurring tunicamycins T and Compound 2. Moreover, a similar effect is observed for Compound 4 which contains the 2′″,3′″-unsaturated fatty acid chain, but has a 2″-azido group in place of the 2″-acetylamino found on the native tunicamycins. Compound 4 is essentially non-toxic on the model eukaryote, but retains an antibacterial activity that is almost equivalent to the native tunicamycin. Noticeably, the other synthetic tunicamycins in the Baio Yu library (Compounds 1, and 5-10) having other changes to the native tunicamycin structure completely lack antimicrobial activity on either organism. Compound 5 has a N-phthaloyl protecting group in place of the N-linked fatty acid chain, and Compounds 1, 6 and 9 lacks a fatty acid chain entirely. Also noticeable is that Compounds 6, 7, 8, and 10 have no antimicrobial biological activity. Compounds 6, 7, and 8 have a p-methoxyphenol protecting group in place of the N-uracil of native tunicamycin; and for Compound 10, the N-uracil is replaced by N-adenine.

EXAMPLE 2

Eukaryotic Protein N-glycosylation Assay on Chemically-synthesized Tunicamycins Using a *Pichia* Yeast-based Assay Based on the results of the QSAR antimicrobial assay described above, Compound 3 and Compound 4 have reduced toxicity on the model eukaryote (yeast) relative to native tunicamycins. Because the mechanism for the toxicity of tunicamycins towards eukaryotes occurs via inhibition of the first step of protein N-glycosylation (see, e.g., Heifetz, et al., *Biochemistry* 18:2186-2192 (1979)), the synthetic tunicamycins (Compounds 1 to 10) are tested using a *Pichia*-based assay for protein glycosylation using the assay described in Price, et al. (2016). In this assay, essentially an *Arabidopsis* gene for a known N-glycoprotein (AtchitIV) is altered to include a secretory leader region and is heterologously expressed using a commercially available methanol-inducible promoter system in *Pichia* yeast transformed with an expression vector containing this construct. When grown in culture, this transformed *Pichia* secretes the recombinant AtchitIV N-glycoprotein into the culture medium after methanol induction. This secreted AtchitIV N-glycoprotein is readily isolated by precipitation with ammonium sulfate, separated, and visualized by SDS-PAGE, as described in Price, et al. (2016).

Compounds 1 to 10 described above, naturally-occurring tunicamycin (T, Sigma-Aldrich Inc., St. Louis, Mo.), and DMSO control (C) are compared using this protein glycosylation assay. Compounds 1 to 10 and the naturally-occurring tunicamycin (T, 20 µg/mL) are introduced into the *Pichia* cultures after 8 days growth at the same stage as the induction of AtchitIV5 expression by the addition of methanol. With DMSO (no inhibitor control C) added to the *Pichia* culture, the AtchitIV5 protein appears on SDS-PAGE as a series of diffuse bands ranging in size from approximately 35 kDa to approximately 50 kDa which occurs because of multiple N-glycosylation forms. Addition of naturally-occurring tunicamycin (T) to the *Pichia* culture results in a single band of ~30 kDa on the SDS-PAGE, corresponding to the non-glycosylated form of AtchitIV5; thus demonstrating that tunicamycin blocks the N-glycosylation of AtchitIV5. Similarly, Compound 2 has the same effect as the naturally occurring tunicamycins, as observed on the SDS-PAGE. Compound 3 results in an approximately 50:50 mixture of the single band of ~30 kDa and the diffuse bands ranging in size from approximately 35 kDa to approximately 50 kDa. Thus, Compound 3, which lacks the 2''',3'''-unsaturated double bond in the N-linked fatty acid, appears to be a less effective inhibitor of AtchitIV5 N-glycosylation. Compounds 1, and 4-10 exhibited no inhibitory activity in this AtchitIV5 N-glycosylation assay. From these results, it is hypothesized that the lack of the 2''',3'''-double bond moiety on tunicamycin significantly lowers the activity to block protein N-glycosylation, and it is this mechanism that lowers the toxicity of the modified tunicamycins towards eukaryotes.

EXAMPLE 3

Chemical modifications to Tunicamyins, Quinovosamycins, and Streptovirudins

Because the QSAR study and the AtchitIV5 N-glycosylation study highlight the importance of 2''',3'''-double bond in the tunicamycin fatty acid chain and that reducing the double bond to a single bond results in less toxicity to the yeast, chemical modifications of tunicamycin of this double bond and the double bond in the uracil group is explored. As mentioned supra, naturally-occurring tunicamycins contain a fatty acid chain that contains an unsaturated 2''',3'''-double bond; i.e., conjugated to the acyl amide carbonyl group. They also contain a uracil group with a second double bond in the uracil ring. However, first tests are conducted on uridine as a model compound to assess how best to reduce the double bond in the uracil group in tunicamycin. Uridine contains an N-linked uracil group analogous to that found in tunicamycin.

20 mg uridine (Sigma-Aldrich Inc., St. Louis, Mo.) is dissolved in methanol:toluene (1:1 v/v, 2 mL), plus one drop of glacial acetic acid (10 µL). A catalytic amount of solid palladium on carbon catalyst (10% Pd/C, 3 mg) (Sigma Aldrich, St. Louis, Mo.) is added followed by an addition of solid sodium borohydride (7 mg) (Sigma Aldrich, St. Louis, Mo.). The purpose of the acetic acid is to keep the pH mildly acidic (pH 4), so that upon addition of sodium borohydride, the sodium borohydride is degraded to produce hydrogen. The duration for the reaction is determined by a time course experiment, analyzing samples every 2 hours by MALDI-TOF mass spectrometry. Similarly, the reaction temperature is determined by undertaking the reaction at 20° C., 40° C., 60° C., or 100° C. After these time points, the reaction is cooled to room temperature, and the reaction mixture is filtered through a small cotton pad plus Celite filter (Sigma Aldrich, St. Louis, Mo.) to remove the spent Pd/C catalyst. The filtrate is dried down on an airline, re-dissolved in methanol (2 mL), and heated at 80° C. for 15 minutes. This step results in the conversion of residual sodium borohydride to methyl borate (which is volatile) and residual acetic acid to methyl acetate (also volatile). These volatiles are removed by evaporation on an airline. The residue is dissolved in deuterated water for analysis by NMR using a Bruker AVANCE III instrument (Billerica, MA) to record the spectrum at 500.11 MHz. Control reactions are run that either lacked the Pd/C catalyst (but included the borohydride), or lacked both Pd/C and the sodium borohydride and/or lacked heating.

Pd/C catalyst in the presence of hydrogen gas is the standard method for the reduction of acyl double bonds, but the use of the gaseous hydrogen is inconvenient, especially on scale-up. The use of sodium borohydride plus acetic acid to generate the hydrogen in situ, in the presence of the Pd/C catalyst, has been prescribed by Amezcua, et al., *Int. J. Undergrad. Res. Creative Acts* 7, Art. 5 (2015). Amezcua, et al., demonstrated that 30 minutes at room temperature is sufficient to reduced C=C double bonds of α,β-carbonyl compounds (fatty acid, esters, amide, etc.). However, the extended reaction conditions (time (50 hour) and temperature (60° C.)) that are required to give quantitative reduction of the uracil group have not been described previously. This reaction condition is determined by running the reduction reaction at 60° C. for a time course, removing samples every 2 hours and analyzing the generated compounds by MALDI-TOF mass spectrometry. In this MALDI-TOF MS-based assay, the reduction of the acyl double bond is observed as a 2 Da increase in molecular mass (FIG. 6B), and reduction of both double bonds results in a 4 Da mass increase (FIG. 6C). Moreover, the Celite filtration followed by methanol esterification to converted residual borate and acetic acids to their easy-to-remove volatile esters have also not been described previously, but these procedures are used in the analysis of sugars (for examples, see Chapman & Kennedy, IRL Press, 1986).

Figure 5A:
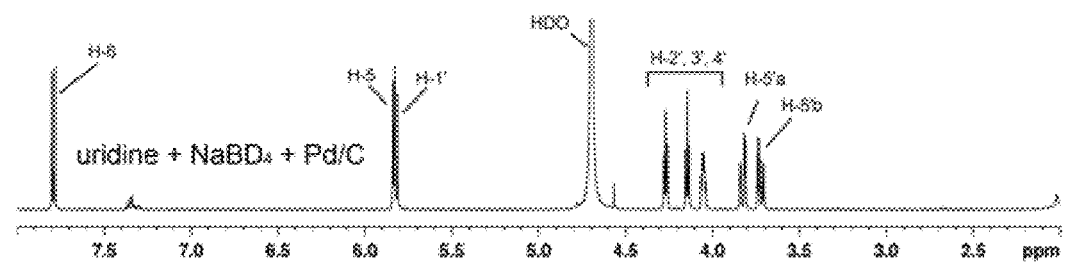
FIG. 5A shows the proton NMR spectra of the model compound uridine after treatment with $NaBH_4$ and Pd/C catalyst, but without heating. Characteristic signals for the uracil double bond signals (H-5 and H-6), and of the ribosyl ring (H1'-H5'a,b) are shown.
Figure 5B:
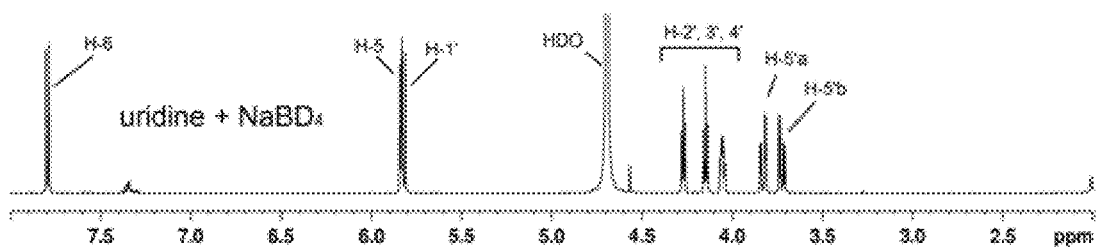
FIG. 5B shows the proton NMR spectra of the model compound uridine after treatment with $NaBH_4$ but without the Pd/C catalyst. Characteristic signals for the uracil double bond signals (H-5 and H-6), and of the ribosyl ring (H1'-H5'a,b) are shown.

FIG. 5A shows the proton NMR spectra of the 2.0-8.0 ppm region of uridine after treatment with NaBH$_4$ and Pd/C catalyst, but without heating. Characteristic signals for the uracil double bond signals (H-5 and H-6), and of the ribosyl ring (H1'-H5'a,b) are shown. No reduction of the uracil double bond is evident. FIG. 5B shows the proton NMR spectra of the 2.0-8.0 ppm region of uridine after treatment with NaBH$_4$ but without the Pd/C catalyst. Characteristic signals for the uracil double bond signals (H-5 and H-6), and of the ribosyl ring (H1'-H5'a,b) are shown. No reduction of the uracil double bond is evident. Thus, in the proton NMR spectra of non-reduced uridine (FIG. 5A and FIG. 5B), uridine H5 and H6 protons are clearly evident at 5.85 ppm and 7.8 ppm, with a J5,6 coupling constant of 8.4 Hz. In the control experiments the H5 peak (5.85 ppm) is overlapped by the ribosyl H-1' anomeric proton at 5.84 ppm ($J_{1',2'}$=4 Hz). The H5 and H6 clearly integrate to 1:1, and correspond with the 1:1:1:1:2 integrations for the ribosyl protons. To summarize, no reduction of the uracil double bond is evident in either experiment without heating or without the Pd/C catalyst.

Figure 5C:
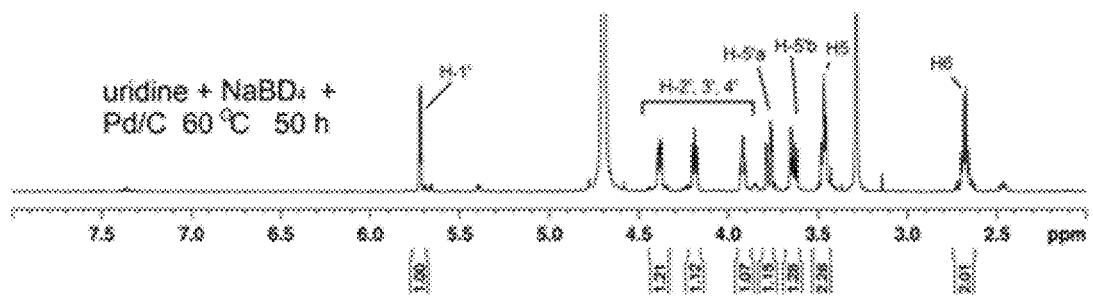
FIG. 5C shows the proton NMR spectra of the model compound uridine after treatment with $NaBH_4$ plus Pd/C catalyst for 50 hours at 60° C. Characteristic signals for the uracil double bond signals (H-5 and H-6), and of the ribosyl ring (H1'-H5'a,b) are shown.

In contrast, FIG. 5C shows the proton NMR spectra of the 2.0-8.0 ppm region of uridine after treatment with $NaBH_4$ plus Pd/C catalyst for 50 hours at 60° C. Characteristic signals for the uracil double bond signals (H-5 and H-6), and of the ribosyl ring (H1'-H5'a,b) are shown. Reduction of the H-5, H-6 uracil double bond is evident from their shifts to 3.45 and 2.68 ppm, respectively. These signals integrate to approximately 2, showing that they have been reduced to $CH_2$ groups. In the uridine reaction with Pd/C plus sodium borohydride, the uridine H5 and H6 protons completely disappear in the NMR spectrum, indicating the complete reduction of the double bond. Moreover, a new peak is now evident at 2.68 ppm, which corresponds to the now reduced $CH_2$'s at positions 5 and 6. When sodium borodeuteride is used as the reducing agent this new peak at 2.68 ppm integrates to 2.01, clear evidence that the double bond is quantitatively reduced. Hence, treatment of uridine with $NaBH_4$ plus Pd/C catalyst for 50 hours at 60° C. results in complete reduction of the uracil double bond.

After determining that this reaction reduces the double bond in uridine, it is used to reduce one of double bonds in tunicamycins, or both double bonds. The reaction described supra is performed with 1 mg tunicamycin (Sigma Aldrich, St. Louis, Mo.). The quantity of sodium borohydride is correspondingly reduced to 1 mg, with the quantity of 10% P/C catalyst kept at 2.5 mol/%. Glacial acetic acid (10 µL) is added as described supra. The reaction is run for either 30 minutes at room temperature or for 50 hours at 60° C. After the reaction period the spent Pd/C catalyst is filtered off through a cotton pad using a Celite filter (Sigma Aldrich, St. Louis, Mo.) as described above, then refluxed with methanol (2 mL, 80° C., 15 minutes) to remove the residual sodium borate (from borohydride) and acetic acid as their volatile methyl esters. The residues containing the reduced tunicamycins are dissolve in deuterated $d_6$-methanol for analysis by MALDI-TOF mass spectrometry using a Bruker-Daltonics Microflex instrument (Billerica, Mass.) using 2,5-DHB as the matrix and proton NMR using a Bruker AVANCE III instrument, recorded at 500.11 MHz (see infra). The numbering system for the tunicamycins is described by Tsvetanova and Price, J. Antibiot. 60:485-491 (2007).

Figure 6A:
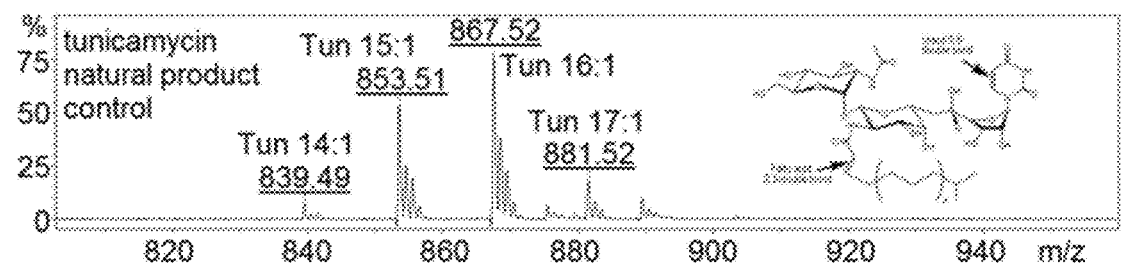
FIG. 6A shows the matrix-assisted laser desorption/ionization (MALDI) mass spectrometry of unmodified tunicamycins (the natural product controls). The ion peaks labeled Tun 14:1, Tun 15:1, Tun 16: 1, and Tun 17:1 correspond to the components of native tunicamycins, with increasing fatty acid chain length (n=14, 15, 16, or 17) and one 2,3-acyl double bond, plus the uracil 5,6-double bond (indicated by arrows).
Figure 6B:
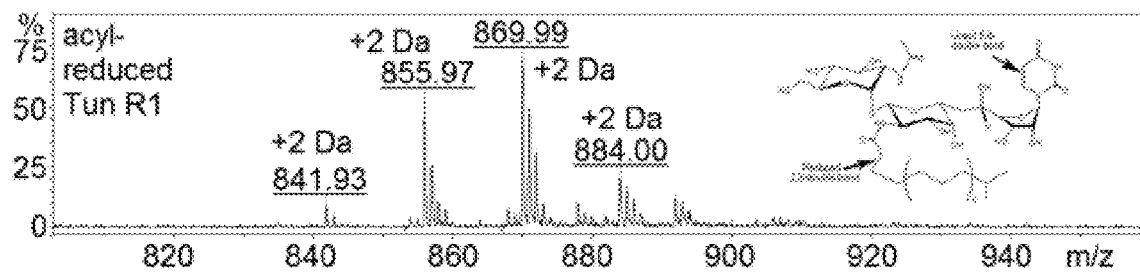
FIG. 6B shows the MALDI mass spectrometry of tunicamycin related compounds—acyl-reduced (referred to alternatively as "R1" and "Tun-R1"). The ion peaks correspond to with mass increases of +2 Da (in Tun-R1 compounds) corresponds to the reduction of the 2,3-fatty acid double bonds only (i.e., the insertion of two H atoms).
Figure 6C:
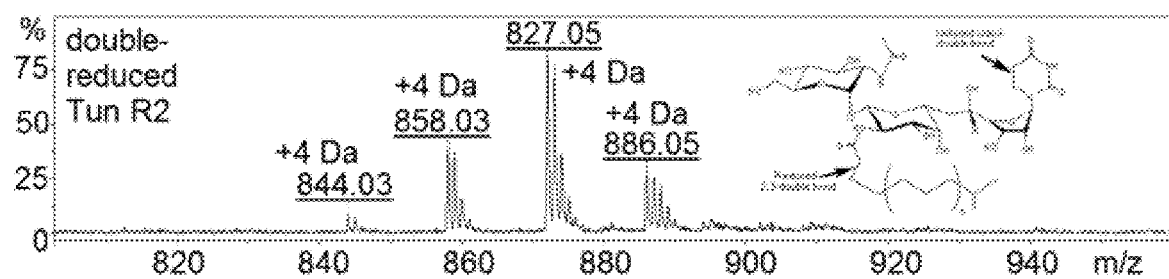
FIG. 6C shows the MALDI mass spectrometry of tunicamycin related compounds—double reduced (referred to alternatively as "R2" and "Tun-R2"). The ion peaks correspond with the mass increases of +4 Da (in Tun-R2 compounds) corresponds to the reduction of the 2,3-fatty acid double bond and the uracil double bond (i.e., the insertion of four H atoms).

FIG. 6A shows the matrix-assisted laser desorption/ionization (MALDI) mass spectrometry of unmodified tunicamycins (the natural product controls). The ion peaks labeled Tun 14 (m/z 839.49), Tun 15:1 (m/z 853.51), Tun 16:1 (m/z 867.52), and Tun 17:1 (m/z 881.52) correspond to the components of native tunicamycins, with increasing fatty acid chain length (n=14, 15, 16, or 17). These native tunicamycins have one 2,3-acyl double bond, plus the uracil 5,6-double bond (indicated by arrows). FIG. 6B shows the MALDI-TOF mass spectrometry of the modified tunicamycin related compounds Tun-R1-acyl-reduced. These Tun-R1 compounds are produced in a reaction at room temperature for 30 minutes. The ion peaks labelled m/z 841.93, m/z 855.97, m/z 869.99, and m/z 884.00 correspond to the acyl reduced tunicamycins (Tun-R1), with increasing fatty acid chain length (n=14, 15, 16, or 17). The mass increases of +2 Da in Tun-R1 compounds correspond to the reduction of the 2,3-fatty acid double bonds (i.e., the insertion of two H atoms). FIG. 6C shows MALDI-TOF mass spectrometry of tunicamycin related compounds Tun-R2-double reduced. These Tun-R2 compounds are produced in a reaction at 60° C. for 50 hours. The ion peaks labeled m/z 844.03, m/z 858.03, m/z 827.05 and m/z 886.05 correspond to the components of Tun-R2 (double-reduced) with increasing fatty acid chain length (n=14, 15, 16, or 17). The mass increases of +4 Da in the Tun-R2 compounds correspond to the reduction of the 2,3-fatty acid double bonds and the double bond in the uracil group (i.e., the insertion of four H atoms).

Figure 7A:
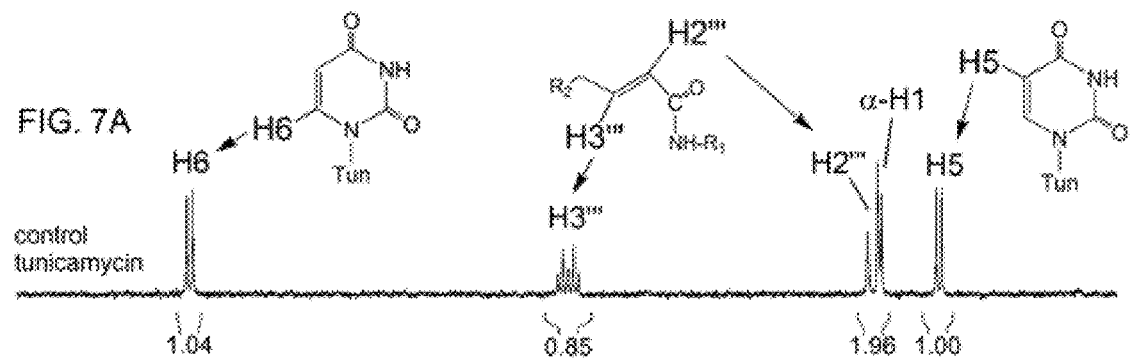
FIG. 7A shows the proton NMR spectra of the unmodified natural product tunicamycins. Characteristic signals for the tunicamycin N-acyl double bond protons (H-2''' and H-3'''), the uracil double bond signals (H-5 and H-6), and the alpha-H-1' anomeric signal on the tunicamine ring are shown.
Figure 7B:
FIG. 7B shows the proton NMR spectra of the acyl-reduced tunicamycin related compounds, Tun-R1. Characteristic signals for the tunicamycin N-acyl double bond H-2''' and H-3''' protons (as seen in FIG. 7A) disappear after the reaction for 30 minutes at 24° C. indicating reduction of the double bond. The uracil H-5 and H-6, and the tunicamine alpha-H-1' anomeric proton remain unchanged by the reaction condition.
Figure 7C:
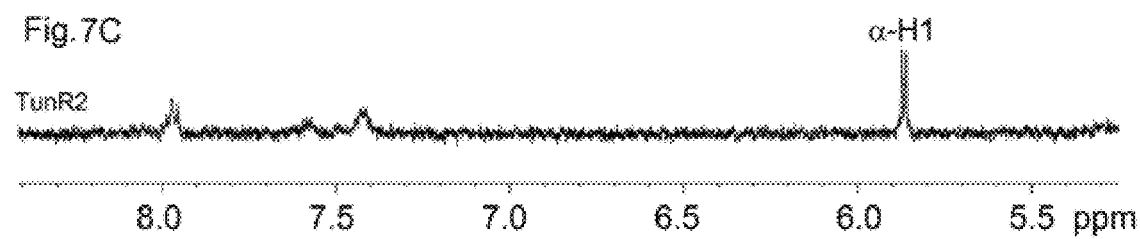
FIG. 7C shows the proton NMR spectra of the double-reduced tunicamycin related compounds, Tun-R2. Characteristic signals for the tunicamycin N-acyl double bond H-2''' and H-3''' protons and the uracil H-5 and H-6 signals disappear after 50 hours at 60° C., showing that the double reduction has occurred. The alpha-H-1' anomeric signal of the tunicamine ring is unaffected by the reductions.

FIG. 7A shows the proton NMR spectra of the 5.6-8.2 ppm region of the unmodified natural product tunicamycins. Characteristic signals for the tunicamycin N-acyl double bond protons (H-2''' and H-3'''), the uracil double bond signals (H-5 and H-6), and the alpha-H-1' anomeric signal on the tunicamine ring are shown. FIG. 7B shows the proton NMR spectra of the 5.6-8.2 ppm region of the acyl-reduced tunicamycin related compounds, Tun-R1. Characteristic signals for the tunicamycin N-acyl double bond H-2''' and H-3''' protons (as seen in FIG. 7A) disappear after the reaction for 30 minutes at 24° C. indicating reduction of the double bond. The uracil H-5 and H-6, and the tunicamine alpha-H-1' anomeric proton remain unchanged by the reaction conditions. FIG. 7C shows the proton NMR spectra of the 5.6-8.2 ppm region of the double-reduced tunicamycin related compounds, Tun-R2. Characteristic signals for the tunicamycin N-acyl double bond H-2''' and H-3''' protons and the uracil H-5 and H-6 signals have disappeared after 50 hours at 60° C., showing that the double reduction has occurred. The alpha-H-1' anomeric signal in unchanged because the tunicamine ring is unaffected by the reduction reaction.

Figure 4A:
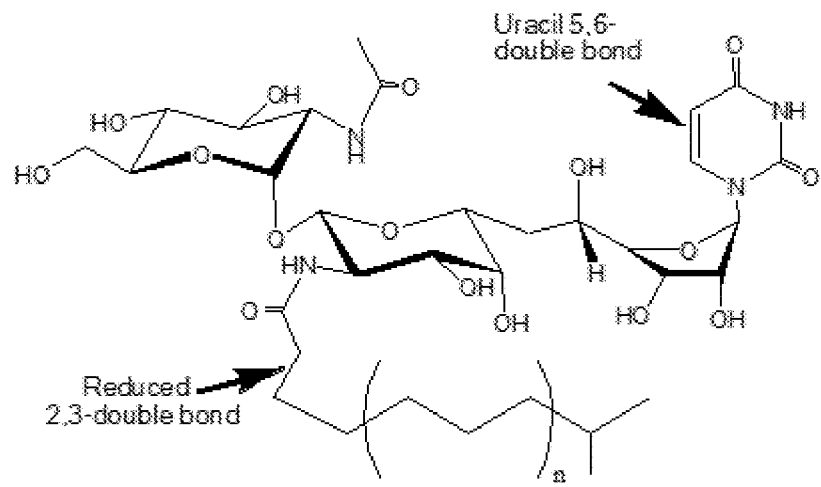
FIG. 4A shows the chemical structure of single reduced tunicamycins (referred to as "Tun-R1") in which the fatty acid acyl chain's length can vary and its 2''',3'''-double bond is reduced.
Figure 4B:
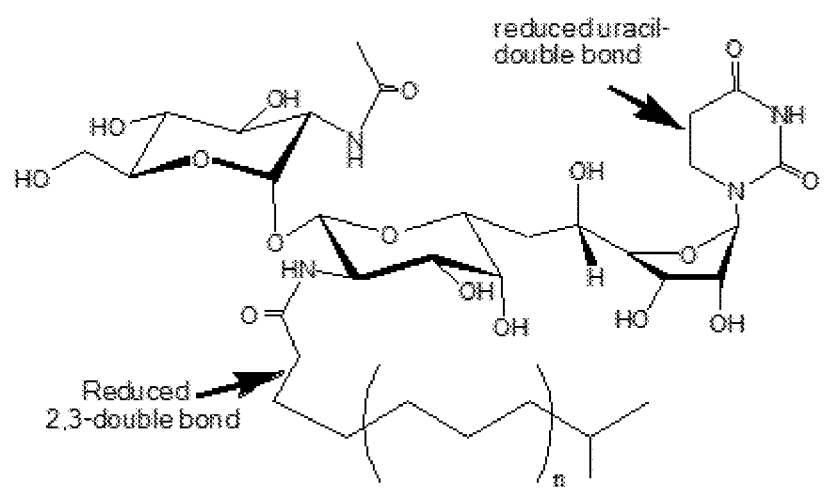
FIG. 4B shows the chemical structure of double reduced tunicamycins (referred to as "Tun-R2") in which the fatty acid acyl chain's length can vary and its 2''',3'''-double bond and the uracil 5,6-double bond are both reduced.
Figure 4C:
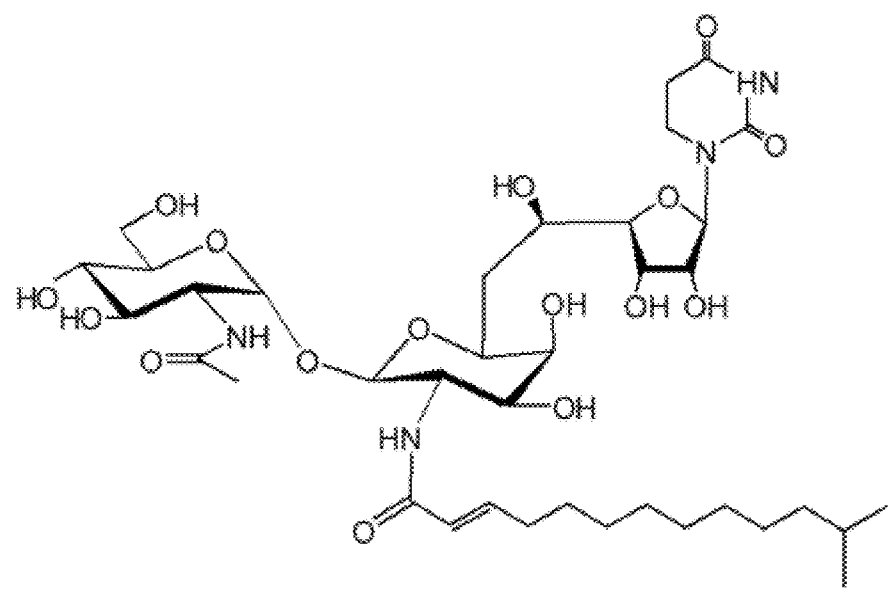
FIG. 4C shows the chemical structure of a specific, naturally-occurring streptovirudin ("Tun-R3") which the uracil 5,6-bond is fully reduced and the fatty acid acyl chain contains a double bond at the 2''',3''' position.

Based on the above assays, it is evident that two types of tunicamycin related compounds are made, Tun-R1 (see Formula 1 supra) and Tun-R2 (see Formula 2 supra), which are shown in FIG. 4A and FIG. 4B, respectively. Tun-R1 (single reduced tunicamycins) are produced by reducing the 2''',3'''-double bond in the fatty acid chains using the above described reduction reaction performed over a short time (approximately 30 minutes) at ambient temperature (approximately 24° C.). Tun-R2 (double reduced tunicamycins) are produced by reducing both the 2''',3'''-acyl double bond and the 5,6-double bond in the uracil ring using a reduction reaction performed over a prolonged period of time (approximately 50 hours) at a high temperature (approximately 60° C.). Other chemical reductions of double bonds that may be suitable for this reaction are catalytic hydrogenation with hydrogen gas, typically catalyzed by a precious metal catalyst (often platinum, palladium, rhodium, or ruthenium), transfer hydrogenation (typically using hydrazine or formic acid), or electrolytic hydrogenation. See Johnstone, et al., Chem. Rev., 85:129-170 (1985). Tun-R1 and Tun-R2 are next tested for reduced toxicity to eukaryotic cells and while retaining toxicity to bacterial cells.

EXAMPLE 4

Biological Assays of Tun-R1 and Tun-R2

Tun-R1 and Tun-R2 are tested for antimicrobial activity against Bacillus subtilis (Gram-positive bacterium) and against S. cerevisiae (eukaryote) in an agar diffusion-zone of inhibition assay described above in which 0.5 µg of naturally-occurring tunicamycins, Tun-R1, or Tun-R2 are added to 5 µL wells in the agar. Naturally-occurring tunicamycins (Sigma Aldrich, St. Louis, Mo.) produce a zone of clearing of ~2.5 cm against both *B. subtilis* and *S. cerevisiae*. Both Tun-R1 and Tun-R2 produce similar zones of clearing on the *B. subtilis* plate. Tun-R1 causes a zone of clearing of ~0.3 cm on the S. cerevisiae plate; approximately 10-fold less toxicity to yeast than the naturally occurring tunicamycins. Even more dramatically, and unexpectedly, Tun-R2 is completely non-toxic against *S. cerevisiae*, evidenced by no zone of clearing on the *S. cerevisiae* plate even though Tun-R2 produces a zone of clearing of ~2.5 cm on the *B. subtilis* plate.

Quantitative broth dilution assays are performed on broth dilutions of *Bacillus subtilis* and *S. cerevisiae* to assess the minimum inhibitory concentrations (MICs) of Tun-R1 and Tun-R2 on these microorganisms. In the microtiter plate broth dilution assays, the naturally occurring tunicamycins has MICs of 0.15 µg/mL and 0.3 µg/mL on *B. subtilis* and *S. cerevisiae*, respectively. Determination of MIC is generated visually because the microorganisms grow into a cell pellet at the bottom of the wells. Lack of a pellet indicates inhibition of cell growth. Tun-R1 has similar antibacterial activity on *B. subtilis* (MIC of 0.3 µg/mL), and has reduced activity on S. cerevisiae (MIC of 2.5 µg/mL). Tun-R2 also has a similar antibacterial activity on *B. subtilis* (MIC of 0.3 µg/mL), but it is effectively non-toxic (MIC>10 µg/mL) against *S. cerevisiae*. Hence, these broth dilution assays confirm the agar diffusion assay results, and demonstrate that Tun-R1 and Tun-R2 possess greatly reduced toxicity against eukaryotes while retaining their antibacterial activity.

Figure 9A:
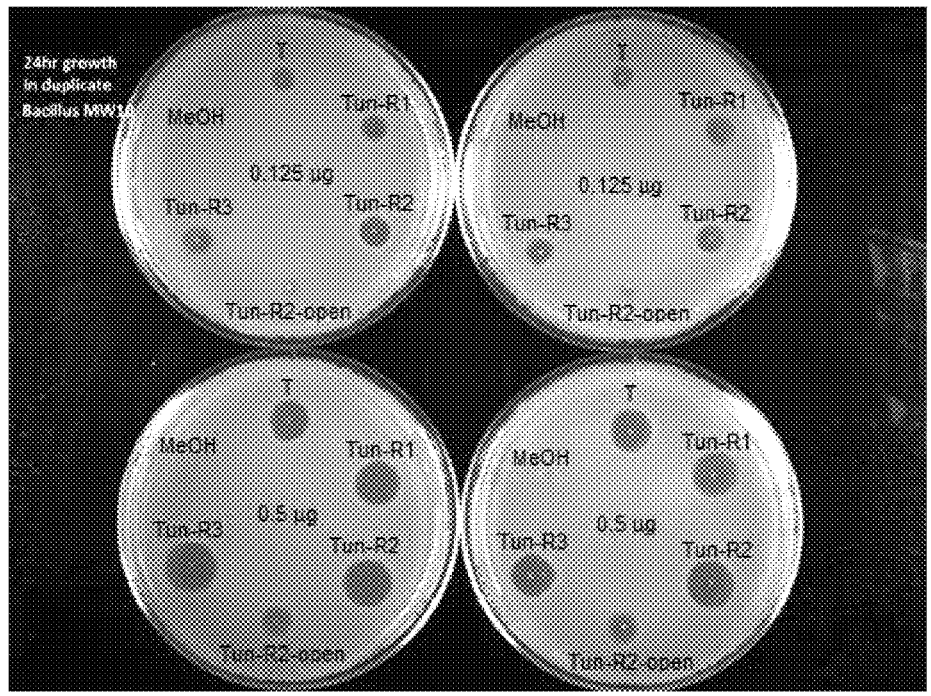
FIG. 9A compares the activity against *Bacillus subtilis* strain MW10 of 0.125 µg (top plates) or 0.5 µg (bottom plates) of naturally-occurring tunicamycins (T), a mixture of Tun-R1 compounds with varying fatty acid acyl chain length (labeled Tun-R1) (see Formula 1), a mixture of Tun-R2 compounds with varying fatty acid acyl chain length (labeled Tun-R2) (see Formula 2), modified tunicamycin compounds with varying fatty acid acyl chain length (fully saturated) and an opened uracil ring (labeled Tun-R2-open; uracil ring was opened via base hydrolysis), a mixture of streptovirudin compounds of varying fatty acid acyl chain length, where the fatty acid acyl chain contains a single double bond and the uracil ring contains only single bonds (labeled Tun-R3), and methyl alcohol (MeOH, negative control).
Figure 9B:
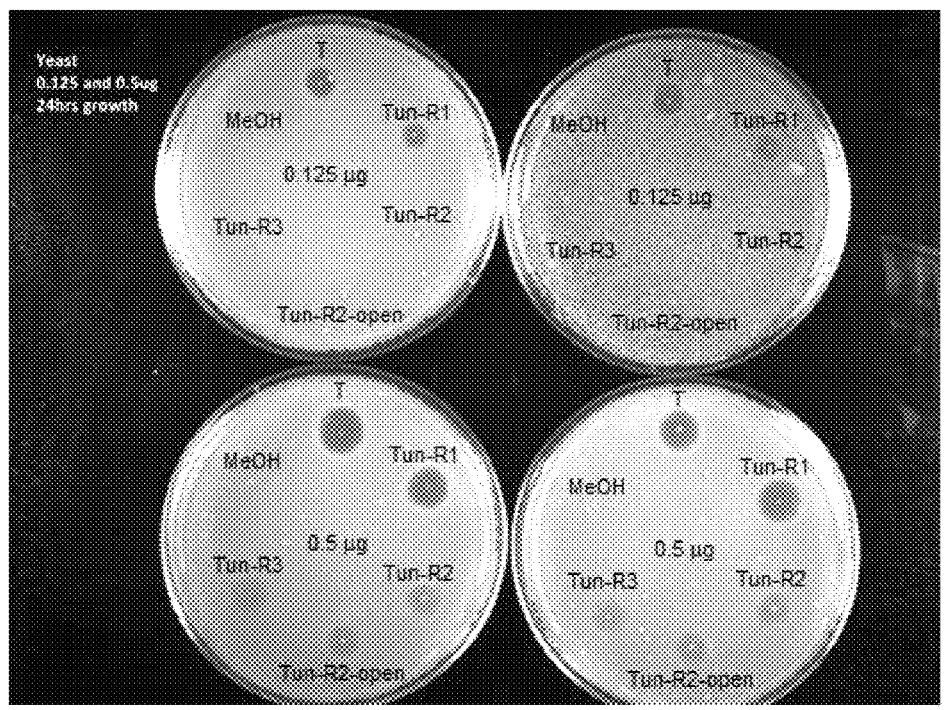
FIG. 9B compares the activity against *Saccharomyces cerevisiae* of 0.125 µg (top plates) or 0.5 µg (bottom plates) of the same compounds as in FIG. 9A.

Next, the killing activity (MIC) of a mixture of streptovirudin compounds of varying fatty acid acyl chain length, where the fatty acid acyl chain contains one double bond and the uracil ring contains only single bonds (labeled Tun-R3) (see FIG. 4C and Formula 3, supra), is compared to the killing activity (MIC) of naturally-occurring tunicamycins (T), a mixture of Tun-R1 compounds with varying fatty acid acyl chain length (labeled Tun-R1) (see Formula 1), a mixture of Tun-R2 compounds with varying fatty acid acyl chain length (labeled Tun-R2) (see Formula 2), modified tunicamycin compounds with varying fatty acid acyl chain length (fully saturated), an opened uracil ring (labeled Tun-R2-open; uracil ring was opened via base hydrolysis), and methyl alcohol (MeOH) as negative control. The streptovirudin compounds (Tun-R3) are produced by *Streptomyces* spp. NRRL Accession F-4474. FIG. 9A shows duplicate agar plates (left and right top; left and right bottom) containing a lawn of *Bacillus subtilis* strain MW10 with the compounds applied to the wells at 0.125 µg (top plates) or 0.5 µg (bottom plates). The streptovirudin compounds (Tun-R3) kill *B. subtilis* strain MW10 approximately equally well as naturally-occurring tunicamycin compounds (T), Tun-R1 compounds (Tun-R1), and Tun-R2 compounds (Tun-R2). The opened uracil ring tunicamycin compounds (Tun-R2-open) are less effective at killing *B. subtilis* strain MW10. FIG. 9B shows duplicate agar plates (left and right top; left and right bottom) containing a lawn of *Saccharomyces cerevisiae* with the compounds applied to the wells at 0.125 µg (top plates) or 0.5 µg (bottom plates). In FIG. 9B, the streptovirudin compounds (Tun-R3), opened uracil ring tunicamycin compounds (Tun-R2-open), and Tun-R2 compounds (Tun-R2) have no effect on *S. cerevisiae* at 0.125 µg (top plates) and very little killing of *S. cerevisiae* at 0.5 µg (bottom plates). In comparison, the naturally-occurring tunimycin compounds (T) and Tun-R1 compounds (Tun-R1) effectively kill *S. cerevisiae* at 0.125 µg (top plates) and at 0.5 µg (bottom plates). This experiment demonstrates that the streptovirudin compounds (Tun-R3) and the Tun-R2 compounds (Tun-R2) can be safely administered to eukaryotes (including animals) at 0.125 µg and possibly 0.5 µg and still kill gram-positive bacteria.

EXAMPLE 5

Reduction of the Double Bonds in Tunicamycin Related Compounds (Tun-R1 and Tun-R2) Attenuates Their Inhibitory Activity Toward Eukaryotic Protein N-gvlycosylation Using the transformed *Pichia*-based protein glycosylation assay (Price, et al. (2016)) described above, Tun-R1 and Tun-R2 are compared to naturally occurring tunicamycins for eukaryotic N-glycosylation inhibition. As described above, in the negative control experiment in which DMSO is added to transformed *Pichia* culture, a series of bands of N-glycosylated AtchitIV5 glycoprotein ranging between approximately 35 kDa to approximately 50 kDa are produced. Addition of 20 µg/mL tunicamycin (T) to transformed *Pichia* culture completely inhibits N-glycosylation of AtchitIV5, as evidenced by a non-glycosylated protein band at approximately 33 kDa. Under identical conditions (20 µg/mL; 8 hour exposure), Tun-R1 inhibits AtchitIV5 N-glycosylation at approximately 50% of the amount observed for naturally occurring tunicamycin, as evidenced by the band at approximately 33 kDa being approximately equal intensity to the series of bands between approximately 35 kDa and approximately 50 kDa in the negative control (DMSO) lane. The double-reduced Tun-R2 demonstrates no inhibition of protein glycosylation in this assay, as evidenced by the series of AtchitIV5 glycoprotein bands between approximately 35 kDa and approximately 50 kDa. Thus, Tun-R1 has reduced inhibitory activity in the protein N-glycosylation assay, and Tun-R2 is completely inactive, concomitant with the reduced toxicity of these tunicamycin related compounds against eukaryotic cells. This example demonstrates that the lowering of eukaryotic toxicity of Tun-R1 and Tun-R2 results from the attenuated and null (respectively) to reduce N-glycosylation of eukaryotic glycoproteins.

EXAMPLE 6

Activity of Tunicamycin Related Compounds Against Mammalian Cell Lines

Based on the above data that Tun-R1 (having reduction at the 2''',3'''-fatty acid double bond) and Tun-R2 (having reduction at both the 2''',3'''-fatty acid double bond and the 5,6-uracil double bond) exhibit less toxicity against yeast compared to naturally occurring tunicamycins, experiments are conducted to evaluate the comparative cytotoxicity of naturally occurring tunicamycins, structurally related quinovosamycin, Tun-R1, and Tun-R2 against mammalian cells lines in culture. Chinese hamster ovary (CHO) cells are chosen for this experiment because they have been used previously as a model for tunicamycin toxicity. See, e.g., Scocca and Krag, *J. Biol. Chem.*, 265:20621-20626 (1990). A human cell line (MDA-MB-231 triple negative human breast cancer cells) are also used because their known susceptibility to tunicamycin. See, Banerjee, et al., *Cancer*

Res. 71:2095 (2011). The protocols used are described in Duksin & Bornstein, *Proc. Natl. Acad. Sci. (U.S.A.)*, 74:3433-3437 (1977).

Figure 8A:
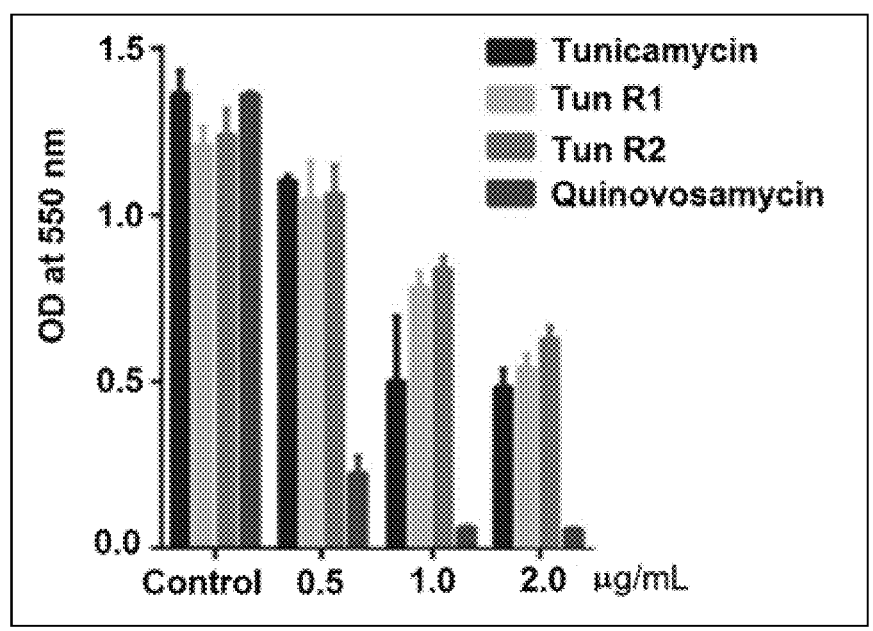
FIG. 8A shows the relative toxicity of tunicamycin, Tun-R1, Tun-R2, and quinovosamycin at 0.5 µg, 1.0 µg, and 2.0 µg to Chinese Hamster Ovary (CHO) cells.
Figure 8B:
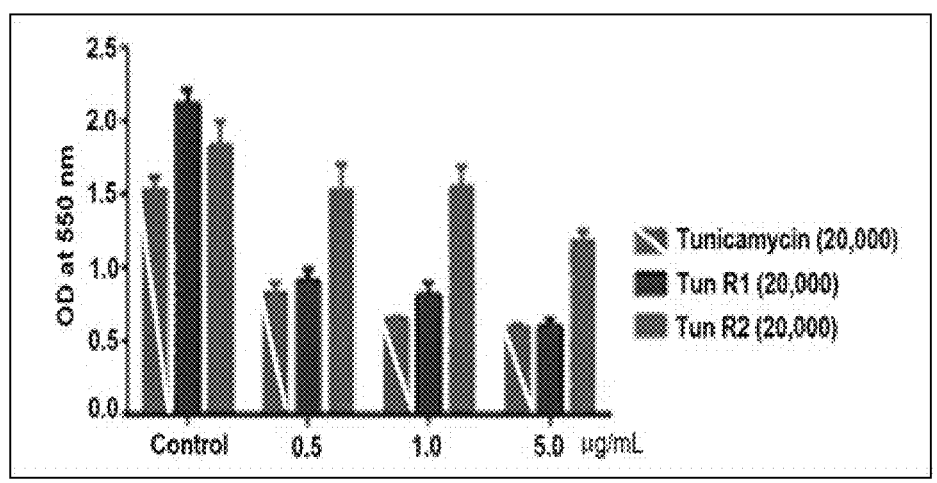
FIG. 8B shows the relative toxicity of tunicamycin, Tun-R1, and Tun-R2 at 0.5 µg, 1.0 µg, and 5.0 µg to MDA-MB-231 human cells.

As expected, naturally occurring tunicamycin, and especially quinovosamycin, are toxic to CHO cells, but Tun-R1 and Tun-R2 surprisingly have significantly reduced toxicity. See FIG. 8A. Against the human MDA-MB-231 cells, native tunicamycin and Tun-R1 have similar toxicity, but Tun-R2 is non-toxic up to 1.0 µg/mL, and has significantly reduced toxicity even at 5.0 µg/mL. See FIG. 8B. Hence, the tunicamycin related compounds, Tun-R1 and Tun-R2, surprisingly have significantly reduced toxicity against one mammalian cell line, while Tun-R2 is surprisingly essentially non-toxic against MDA-MB-231 human breast cancer cells.

EXAMPLE 7

Tunicamycin Related Compounds Synergistically Enhance Activity of Beta-lactam Antibiotics (Penicillins) Against Gram-positive Bacteria Lee, et al. (2016) and others have shown that tunicamycins enhanced the antibacterial of the penicillin antibiotics, even against bacteria that are resistant to penicillin, by inhibition of the teichoic acid biosynthetic enzyme TagO. Campbell, et al. (2011) demonstrated that tunicamycin at 0.4 µg/mL enhances the activity of oxacillin by 64-128 fold against three different MRSA strains. Similarly, the activity of the clinically important beta-lactam, methicillin, is enhanced 16-32 fold, with enhancements also observed for several cephalosporins and penems. Campbell, et al. (2011). However, Lee, et al. (2016) also demonstrated that natural tunicamycins are too toxic to the host mammalian cells to be used for the purpose of penicillin enhancers. Having created two tunicamycin related compounds (Tun-R1 and Tun-R2) with reduced toxicity to yeast, CHO cells, MDA-MB-231 cells, assays are conducted to determine if Tun-R1 and/or Tun-R2 enhances the antibacterial activity of the penicillins.

Using *B. subtilis* strain MW10 as a reporter strain, naturally occurring tunicamycins, Tun-R1, and Tun-R2 are tested as enhancers of oxacillin, methicillin, and penicillin G. The assays are undertaken by broth dilutions of the beta-lactams in microtiter plates, using a live/dead stain (resazurin) to determine the minimal inhibitory concentrations (MICs). See, Wiegand, et al., *Nat. Protoc.* 3:163-175 (2008) and Elshikh, et al., *Biotechnol. Lett.* 38:1015-1019 (2016) for the experimental protocol. The concentration of the Tun-R1 and Tun-R2 (0.4 µg/mL) is 10-fold less than the toxicity observed on MDA-MB-231 cells (supra), and also less than the amount required for antimicrobial activity on yeast cells.

MICs for oxacillin, methicillin, and penicillin G, without any tunicamycins or tunicamycin related compounds added, is 0.25 µg/mL, 0.125 µg/mL, and 0.025 µg/mL, respectively. The addition of naturally occurring tunicamycins improves these MICs to 0.008 µg/mL, 0.031 µg/mL, and 0.0062 µg/mL, respectively, for the three beta-lactams. Similar improvement of the beta-lactam MICs are observed with Tun-R1 and Tun-R2, as with naturally occurring tunicamycins. Hence, MICs for oxacillin, methicillin, and penicillin G are lowered to 0.008 µg/mL, 0.031 µg/mL, and 0.0062 µg/mL, respectively, by the addition of Tun-R1 (0.4 µg/mL), and to 0.008 µg/mL, 0.062 µg/mL, and 0.0062 µg/mL, respectively, by the addition of Tun-R2 (0.4 µg/mL). Surprisingly, against *B. subtilis*, Tun-R1 and Tun-R2 lowers oxacillin's MIC by 32-fold; methicillin's MIC by 4-fold; and penicillin G's MIC by 2-fold. This synergistic effect is surprising. Because of the considerably reduced mammalian toxicity of these tunicamycin related compounds (Tun-R1 and Tun-R2), they are highly suitable as non-toxic, synergic enhancers for combination therapies with the beta-lactam family of antibiotics and other antibiotics.

Using the protocol described above with *B. subtilis* strain MW10 as a reporter strain grown in microtiter plates and resazurin to easily identify live or dead bacteria, the MIC of oxacillin in DMSO (alone) or in combination with native tunicamycin, Tun-R3, or Tun-R2-open against *Bacillus subtilis* is determined. The synergistic effect of 0.4 µg/mL Tun-R3 is very similar to that of 0.2 µg/mL native tunicamycin, lowering oxacillin's MIC from 0.125 µg/mL (oxacillin only) to 0.004 µg/mL (oxacillin and tunicamycin or Tun-R3). Hence, Tun-R3 also enhances the MIC of oxacillin by 32-fold. By contrast, the open-ring compound Tun-R2-open, in which the dihydrouracil ring has been opened by base hydrolysis, shows no enhancement of oxacillin's antibacterial activity. Not wishing to be bound to any hypothesis, the intact urydyl ring appears to be necessary for the enhancement of beta-lactam antibiotics, and that Tun-R3 is also suitable as a non-toxic, synergistic enhancer of the beta-lactam family of antibiotics.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

I, the inventor, claim as follows:

1. A tunicamycin related compound comprising Formula 2

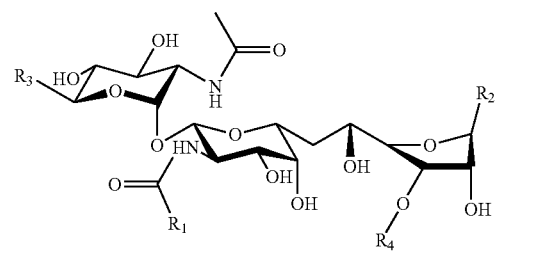

Formula 2 wherein $R_2$ is Y

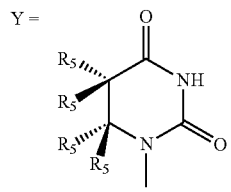

$Y =$ wherein $R_1$ is independently
(i) $CH_3-(CH_2)_n-CH_2-CH_2-$ and n is independently any integer from 9 to 15, or (ii) $CH_3-CH_2-CH(CH_3)(CH_2)_n-CH_2-CH_2-$ and n is independently any integer from 6 to 12;
wherein $R_2$ is Y;
wherein $R_3$ is independently $HOCH_2-$, an alkyl hydrocarbon, or a non-alkyl $C_{1-10}$ hydrocarbon;
wherein $R_4$ is independently H or $P-(O)(OH)_2$; and
wherein $R_5$ is independently H, F, Cl, Br, I, an alkyl hydrocarbon, or a non-alkyl $C_{1-10}$ hydrocarbon.

2. An antibacterial composition comprising at least one of said tunicamycin related compounds of claim 1.

3. The antibacterial composition of claim 2, further comprising an antibiotic, wherein said antibiotic is a β-lactam antibiotic, a non-β-lactam antibiotic, or combination thereof.

4. The antibacterial composition of claim 3, wherein the antibiotic is a β-lactam antibiotic and said β-lactam antibiotic is selected from the group consisting of a penicillin, a cephalosporin, a monobactam, a carbapenem, and a combination thereof.

5. A method of killing Gram-positive bacteria in or on an animal comprising administering to said animal an effective amount of said antibacterial composition of claim 2.

6. The method of claim 5, wherein said antibacterial composition of claim 2 further comprises an antibiotic, wherein said antibiotic is a β-lactam antibiotic, a non-β-lactam antibiotic, or combination thereof.

7. The method of claim 6, wherein said β-lactam antibiotic is selected from the group consisting of a penicillin, a cephalosporin, a monobactam, a carbapenem, and a combination thereof.

8. A method of inhibiting or treating a bacterial infection caused by Gram-positive bacteria in an animal in need to treatment, said method comprising administering to said animal in need of treatment an effective amount of said antibacterial composition of claim 2.

9. The method of claim 8, wherein said antibacterial composition of claim 2 further comprises an antibiotic, wherein said antibiotic is a β-lactam antibiotic, a non-β-lactam antibiotic, or combination thereof.

10. The method of claim 9, wherein said β-lactam antibiotic is selected from the group consisting of a penicillin, a cephalosporin, a monobactam, a carbapenem, and a combination thereof.

11. A method of disinfecting an object or a surface that has Gram-positive bacteria on said object or said surface comprising applying an effective amount of said tunicamycin related compound of claim 1 to said object or said surface in order to kill said Gram-positive bacteria present on said object or said surface.

12. A method of making a tunicamycin related compound of claim 1 comprising
(a) exposing an unmodified tunicamycin to a sufficient amount of a catalyst and a sufficient amount of an agent that hydrogenates double-bonds to single bonds in acidic organic liquid to create a mixture, and
(b) stirring said mixture for approximately 20 hours to approximately 80 hours at a temperature between approximately 50° C. to approximately 95° C. to reduce double bonds in said unmodified tunicamycin's fatty acid acyl chain and uracil ring, thereby generating unpurified tunicamycin related compound of claim 1.

13. The method of claim 12, further comprising
(c) allowing said unpurified tunicamycin related compound of claim 1 to cool to approximately room temperature, and
(d) separating said catalyst from said unpurified tunicamycin related compound of claim 1 at approximately room temperature to generate a composition of unpurified tunicamycin related compound of claim 1 without said catalyst.

14. The method of claim 13, further comprising
(e) suspending said composition of unpurified tunicamycin related compound of claim 1 without said catalyst in an alcohol, and
(f) heating said alcohol suspended unpurified tunicamycin related compound of claim 1 to a sufficient temperature and for a sufficient time to convert any of said agent that hydrogenates double-bonds to single bonds and any of said acid that are present in said alcohol suspended unpurified tunicamycin related compound of claim 1 into volatile organics which are allowed to evaporate, thereby generating said tunicamycin related compound of claim 1 that is purified.

15. An antibacterial composition comprising:
a tunicamycin related compound; and
an antibiotic, wherein said antibiotic is a β-lactam antibiotic, or a combination of a β-lactam antibiotic and a non-β-lactam antibiotic,
wherein the tunicamycin related compound comprises Formula 2

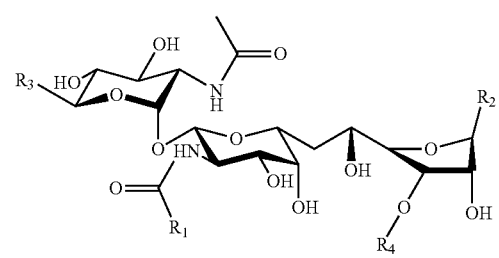

Formula 2 wherein $R_2$ is Y $Y =$

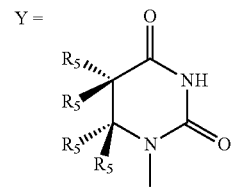

wherein $R_1$ is $(CH_3)_2-CH-(CH_2)_n-CH_2-CH_2-$ and n is independently any integer from 7 to 13;
wherein $R_2$ is Y;
wherein $R_3$ is independently $HOCH_2-$, an alkyl hydrocarbon, or a non-alkyl $C_{1-10}$ hydrocarbon;
wherein $R_4$ is independently H or $P-(O)(OH)_2$; and
wherein $R_5$ is independently H, F, Cl, Br, I, an alkyl hydrocarbon, or a non-alkyl $C_{1-10}$ hydrocarbon.

16. The antibacterial composition of claim 15, wherein the antibiotic is a β-lactam antibiotic and said β-lactam antibiotic is selected from the group consisting of a penicillin, a cephalosporin, a monobactam, a carbapenem, and a combination thereof.

17. A method of killing Gram-positive bacteria in or on an animal comprising administering to said animal an effective amount of said antibacterial composition of claim 15.

18. A method of inhibiting or treating a bacterial infection caused by Gram-positive bacteria in an animal in need to treatment, said method comprising administering to said animal in need of treatment an effective amount of said antibacterial composition of claim 15.

19. A method of disinfecting an object or a surface that has Gram-positive bacteria on said object or said surface comprising applying an effective amount of a tunicamycin related compound to said object or said surface in order to kill said Gram-positive bacteria present on said object or said surface, wherein the tunicamycin related compound comprises Formula 2

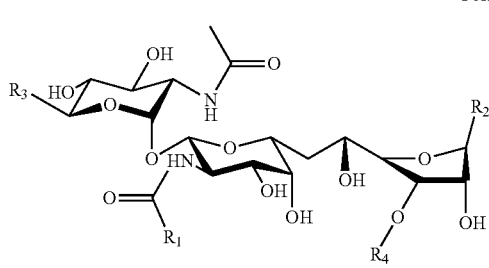

Formula 2 wherein $R_2$ is Y

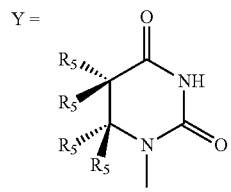

wherein $R_1$ is $(CH_3)_2$—CH—$(CH_2)_n$—$CH_2$—$CH_2$— and n is independently any integer from 7 to 13;
wherein $R_2$ is Y;
wherein $R_3$ is independently $HOCH_2$—, an alkyl hydrocarbon, or a non-alkyl $C_{1-10}$ hydrocarbon;
wherein $R_4$ is independently H or P—(O)(OH)$_2$; and
wherein $R_5$ is independently H, F, Cl, Br, I, an alkyl hydrocarbon, or a non-alkyl $C_{1-10}$ hydrocarbon.

20. A method of making a tunicamycin related compound comprising Formula 2

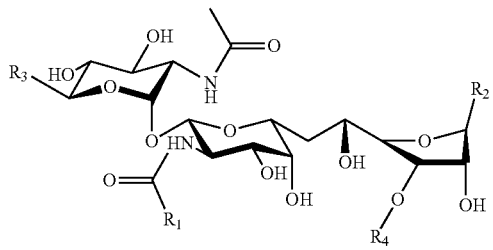

Formula 2 wherein $R_2$ is Y

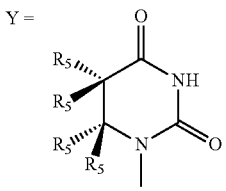

wherein $R_1$ is $(CH_3)_2$—CH—$(CH_2)_n$—$CH_2$—$CH_2$— and n is independently any integer from 7 to 13;
wherein $R_2$ is Y;
wherein $R_3$ is independently $HOCH_2$—, an alkyl hydrocarbon, or a non-alkyl $C_{1-10}$ hydrocarbon;
wherein $R_4$ is independently H or P—(O)(OH)$_2$; and
wherein $R_5$ is independently H, F, Cl, Br, I, an alkyl hydrocarbon, or a non-alkyl $C_{1-10}$ hydrocarbon, the method comprising:
(a) exposing an unmodified tunicamycin to a sufficient amount of a catalyst and a sufficient amount of an agent that hydrogenates double-bonds to single bonds in acidic organic liquid to create a mixture, and
(b) stirring said mixture for approximately 20 hours to approximately 80 hours at a temperature between approximately 50° C. to approximately 95° C. to reduce double bonds in said unmodified tunicamycin's fatty acid acyl chain and uracil ring, thereby generating an unpurified tunicamycin related compound.

21. The method of claim 20, further comprising:
(c) allowing said unpurified tunicamycin related compound to cool to approximately room temperature, and
(d) separating said catalyst from said unpurified tunicamycin related compound at approximately room temperature to generate a composition of unpurified tunicamycin related compound without said catalyst.

22. The method of claim 21, further comprising:
(e) suspending said composition of unpurified tunicamycin related compound without said catalyst in an alcohol, and
(f) heating said alcohol suspended unpurified tunicamycin related compound to a sufficient temperature and for a sufficient time to convert any of said agent that hydrogenates double-bonds to single bonds and any of said acid that are present in said alcohol suspended unpurified tunicamycin related compound into volatile organics which are allowed to evaporate, thereby generating said tunicamycin related compound that is purified.

* * * * *